United States Patent [19]
Smith et al.

[11] Patent Number: 5,759,776
[45] Date of Patent: Jun. 2, 1998

US005759776A

[54] TARGETS FOR BREAST CANCER DIAGNOSIS AND TREATMENT

[75] Inventors: Helene Smith, San Francisco; Ling-Chun Chen, Fremont, both of Calif.

[73] Assignee: California Pacific Medical Center, San Francisco, Calif.

[21] Appl. No.: 463,660

[22] Filed: Jun. 5, 1995

[51] Int. Cl.$^6$ .............................. C12Q 1/68; C12P 19/34; C07H 21/04; C07K 5/00
[52] U.S. Cl. .............................. 435/6; 435/91.2; 435/7.1; 536/22.1; 536/23.1; 536/24.3; 536/24.33; 436/64; 436/94; 530/300; 530/350; 530/388.1
[58] Field of Search .............................. 435/6, 91.2, 7.1; 536/22.1, 23.1, 24.3, 24.33; 436/64, 94; 530/300, 350, 388.1

[56] References Cited

U.S. PATENT DOCUMENTS

| | | |
|---|---|---|
| 4,444,887 | 4/1984 | Hoffman . |
| 4,472,500 | 9/1984 | Milstein et al. . |
| 4,491,632 | 1/1985 | Wands et al. . |
| 4,683,195 | 7/1987 | Mullis et al. . |
| 4,683,202 | 7/1987 | Mullis . |
| 4,968,603 | 11/1990 | Slamon et al. . |
| 5,124,246 | 6/1992 | Urdea et al. . |
| 5,324,654 | 6/1994 | Bredesen . |
| 5,399,346 | 3/1995 | Anderson et al. . |

FOREIGN PATENT DOCUMENTS

| | | |
|---|---|---|
| WO 91/02062 | 2/1991 | WIPO . |
| WO 92/13091 | 8/1992 | WIPO . |
| WO 92/21771 | 12/1992 | WIPO . |
| WO 93/05149 | 3/1993 | WIPO . |
| WO 93/08701 | 5/1993 | WIPO . |
| WO 93/13204 | 7/1993 | WIPO . |
| WO 94/00136 | 1/1994 | WIPO . |
| WO 94/00601 | 1/1994 | WIPO . |
| WO 94/17414 | 8/1994 | WIPO . |
| WO 94/28127 | 12/1994 | WIPO . |
| WO 95/05738 | 3/1995 | WIPO . |

OTHER PUBLICATIONS

Adnane et al. "BEK and FLG, two receptors to members of the FGF family, are amplified in subsets of human breast cancers" *Oncogene* (1991) 6:659–663.

Alitalo et al., "Oncogene amplification in tumor cells" *Adv. Cancer Res.* (1986) 47:235–281.

Altschul et al., "Optimal sequence alignment using affine gap costs" *Bull. Math. Bio.* (1986) 48:603–616.

Bauer et al., "Identification of differentially expressed mRNA species by an improved display technique (DDRT-PCR)" *Nucl. Acids Res.* (1993) 21:4274–4280.

Beardsley "Crapshoot: manufacturers gamble on cancer vaccines–again" *Scientific American* (1994) Sep.:102.

Berns et al., "Sporadic amplification of the insulin–like growth factor 1 receptor gene in human breast tumors" *Cancer Res.* (1992) 52:1036–1039.

Bishop, "Molecular themes in oncogenesis" *Cell* (1991) 64:235–248.

Bast, Jr., "Perspectives on the future of cancer markers" *Clin. Chem.* (1993) 29:2444–2451.

Brison, "Gene amplification and tumor progression" *Biochim. Biophys. Acta* (1993) 1155:24–41.

Culver et al., "Gene therapy for cancer" *Trends Genet.* (1994) 10:174–178.

Dutrillaux et al., "Characterization of chromosomal anomalies in human breast cancer" *Cancer Genet. Cytogenet.* (1990) 49:203–217.

Henikoff et al., "Amino acid substitution matrices from protein blocks" *Proc. Natl. Acad. Sci. USA* (1992) 89:10915–10919.

Kallioniemi et al., "Comparative genomic hybridization for molecular cytogenetic analysis of solid tumors" *Science* (1992) 258:818–821.

Kallioniemi et al., "Detection and mapping of amplified DNA sequences in breast cancer by comparative genomic hybridization" *Proc. Natl. Acad. Sci. USA* (1994) 91:2156–2160.

Lippman, "The development of biological therapies for breast cancer" *Science* (1993) 259:631–632.

Liang et al., "Differential display of eukaryotic messenger RNA by means of the polymerase chain reaction" *Science* (1992) 257:967–971.

Liang et al., "Distribution and cloning of eukaryotic mRNAs by means of differential display: refinements and optimization" *Nucl. Acids Res.* (1993) 21:3269–3275.

MacLean et al., "The immune system, cancer antigens and immunotherapy" *Contemp. Oncol.* (Aug./Sep. 1992) pp. 1–7.

Muss et al., "c–erbB–2 expression and response to adjuvant therapy in women with node–positive early breast cancer" *new Engl. J. Med.* (1994) 330:1260–1266.

Morgan et al., "Human gene therapy" *Ann. Rev. Biochem.* (1993) 62:191–217.

(List continued on next page.)

*Primary Examiner*—W. Gary Jones
*Assistant Examiner*—Dianne Rees
*Attorney, Agent, or Firm*—Morrison & Foerster, LLP

[57] ABSTRACT cDNA sequences derived from four novel genes associated with breast cancer are provided. In over about 60% of the cancer cell lines tested, RNA hybridizing with the cDNAs were substantially more abundant than in normal cells. Most of the cell lines also showed a duplication of the corresponding gene, which probably contributed to the increased level of RNA in the cell. However, for each of the four genes, there were some cell lines which had RNA overabundance without gene duplication. This suggests that the gene product is sufficiently important to the cancer process that cells will use several alternative mechanisms to achieve increased expression. The polynucleotides, polypeptides, and antibodies provided by this invention are expected to be particularly useful in diagnosis and treatment of breast cancer. Also provided is a general method for obtaining cDNA with similar properties that may be associated with breast cancer and other malignancies.

28 Claims, 5 Drawing Sheets

OTHER PUBLICATIONS

Roth, "Modulation of oncogene and tumor–suppressor gene expression: a novel strategy for cancer prevention and treatment" *Ann. Surg. Oncol.* (1994) 1:79–86.

Saint–Ruf et al., "Proto–oncogene amplification and homogeneously staining regions in human breast carcinomas" *Genes Chromosomes & Cancer* (1990) 2:18–26.

Slamon et al., "Human breast cancer: correlation of relapse and survival with amplification of the HER–2/neu oncogene" *Science* (1987) 235:178–182.

Schwab et al., "Amplification of cellular oncogenes: a predictor of clinical outcome of human cancer" *Genes Chromosomes & Cancer* (1990) 1:181–193.

Trentmann et al., "Alternative to $^{35}$S as a label for the differential display of eukaryotic messenger RNA" *Science* (1995) 267:1186–1187.

Unsigned, "Synthetic vaccine stabilizes advanced cancer, prolongs survival" *Oncol. News Int.* (1994) 3:1.

Zafrani et al., "Cytogenetic study of breast cancer; clinicopathologic significance of homogeneously staining regions in 84 patients" *Hum. Pathol.* (1992) 23:542–547.

Aziz et al., "The FDA's perspective on the evaluation of tumor marker tests" *Clin. Chem.* (1993) 39:2439–2443.

Cowley et al., "A vaccine for breast cancer?" *Newsweek* (Nov. 1, 1993) p. 68.

Klijn et al., "The clinical significance of epidermal growth factor receptor (EGF–R) in human breast cancer: a review on 5232 patients" *Endocrine Rev.* (1992) 13:3–17.

Lippman, "Growth factors, receptors, and breast cancer" *J. NIH Res.* (1991) 3:59–62.

Melillo, "Conjugate vaccine shows promise as stimulant of specific antibodies" *Internal Medicine World Report* (Jun. 1–14, 1994) p. 40.

Mok et al., "Molecular cloning of differentially expressed genes in human epithelial ovarian cancer" *Gynecologic Oncol.* (1994) 52:247–252.

Unsigned, "Biomira developing test for breast cancer recurrence" *Toronto Globe and Mail* (Jun. 7, 1994). 1 page total, vol. # not relevant , page # not relevant.

Watson et al., "Isolation of differentially expressed sequence tags from human breast cancer" *Cancer Res.* (1994) 54:4598–4602.

Wintersberger, "DNA amplification: New insights into its mechanism" *Chromosoma* (1994) 103:73–81.

Extended Chromosome No. 1(CH1) breast cancer gene nucleotide sequence; protein translation; and GenBank search of nucleotide and protein sequence. Date of search: Sep. 15, 1995, 30 pages total.

Extended Chromosome No. 8 (CH8) breast cancer gene nucleotide sequence; protein translation; and GenBank search of nucleotide and protein sequence. Date of search: Mar. 26, 1996, 68 pages total.

Extended Chromosome No. 13 (CH13) breast cancer gene nucleotide sequence; protein translation; and GenBank search of nucleotide and protein sequence. Date of search: Sep. 29, 1995, 38 pages total.

Extended Chromosome No. 14 (CH14) breast cancer gene nucleotide sequence; protein translation; and GenBank search of nucleotide and protein sequence. Date of search: Aug. 14, 1995, 39 pages total.

EMBL Data Library Accession No. t27279 XP002019978 (1 page total).

EMBL Data Library Accession No. t27279 XP002019979 (1 page total).

Slamon et al., "Studies of the HER–2/neu proto–oncogene in human breast and ovarian cancer" *Science* (1989) 244:707–712.

Chen et al., "Differential expression of human tissue factor in normal mammary epithelial cells and in carcinomas" *Mol. Med.* (1995) 1:153–160.

Bièche et al., "Loss and gain of distinct regions of chromosome 1q in primary breast cancer" *Clinical Cancer Research* (1995) 1:123–127.

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 152 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 3..152

( x i ) SEQUENCE DESCRIPTION: SEQ ID NO:1:

```
GA AAA CAA ATG GAA GAA ATG CAA AAG GCT TTC AAT AAA ACA ATC GTG         47
   Lys Gln Met Glu Glu Met Gln Lys Ala Phe Asn Lys Thr Ile Val
   1               5                   10                  15

AAA CTT CAG AAT ACT TCA AGA ATA GCA GAG GAG CAG GAT CAG CGG CAA        95
Lys Leu Gln Asn Thr Ser Arg Ile Ala Glu Glu Gln Asp Gln Arg Gln
                  20                  25                  30

ACT GAA GCC ATC CAG TTG CTA CAG GCA CAG CTG ACC AAC ATG ACA CAG       143
Thr Glu Ala Ile Gln Leu Leu Gln Ala Gln Leu Thr Asn Met Thr Gln
              35                  40                  45

CTT GTT CAA                                                           152
```

Leu Val Gln
         50

( 2 ) INFORMATION FOR SEQ ID NO:2:

( i ) SEQUENCE CHARACTERISTICS:
        ( A ) LENGTH: 50 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Lys Gln Met Glu Glu Met Gln Lys Ala Phe Asn Lys Thr Ile Val Lys
 1               5                  10                  15

Leu Gln Asn Thr Ser Arg Ile Ala Glu Gln Asp Gln Arg Gln Thr
            20                  25                  30

Glu Ala Ile Gln Leu Leu Gln Ala Gln Leu Thr Asn Met Thr Gln Leu
            35                  40                  45

Val Gln
 50
```

( 2 ) INFORMATION FOR SEQ ID NO:3:

( i ) SEQUENCE CHARACTERISTICS:
        ( A ) LENGTH: 163 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..162

( x i ) SEQUENCE DESCRIPTION: SEQ ID NO:3:

```
GAA CAG GCA AGC AGA TAT GCT ACT GTC AGT GAA AGA GTG CAT GCT CAA    48
Glu Gln Ala Ser Arg Tyr Ala Thr Val Ser Glu Arg Val His Ala Gln
                 55                  60                  65

GTG CAG CAA TTT CTA AAA GAA GGT TAT TTA AGG GAG GAG ATG GTT CTG    96
Val Gln Gln Phe Leu Lys Glu Gly Tyr Leu Arg Glu Glu Met Val Leu
             70                  75                  80

GAC AAT ATC CCA AAG CTT CTG AAC TGC CTG AGA GAC TGC AAT GTT GCC   144
Asp Asn Ile Pro Lys Leu Leu Asn Cys Leu Arg Asp Cys Asn Val Ala
         85                  90                  95

ATC CGA TGG CTG ATG CTT C                                          163
Ile Arg Trp Leu Met Leu
        100
```

( 2 ) INFORMATION FOR SEQ ID NO:4:

( i ) SEQUENCE CHARACTERISTICS:
        ( A ) LENGTH: 54 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Glu Gln Ala Ser Arg Tyr Ala Thr Val Ser Glu Arg Val His Ala Gln
 1               5                  10                  15

Val Gln Gln Phe Leu Lys Glu Gly Tyr Leu Arg Glu Glu Met Val Leu
            20                  25                  30

Asp Asn Ile Pro Lys Leu Leu Asn Cys Leu Arg Asp Cys Asn Val Ala
            35                  40                  45
```

```
Ile Arg Trp Leu Met Leu
    50
```

( 2 ) INFORMATION FOR SEQ ID NO:5:

( i ) SEQUENCE CHARACTERISTICS:
        ( A ) LENGTH: 107 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..105

( x i ) SEQUENCE DESCRIPTION: SEQ ID NO:5:

```
CTC ACA ATG GGC TAC TGG CCA ACA TAC ACG CCC ATG GAA GTG CAC TTA      48
Leu Thr Met Gly Tyr Trp Pro Thr Tyr Thr Pro Met Glu Val His Leu
 55                  60                  65                  70

ACC CCA GAA ATG ATT AAA CTT CAG GAA GTA TTT AAG GCA TTT TAT CTT      96
Thr Pro Glu Met Ile Lys Leu Gln Glu Val Phe Lys Ala Phe Tyr Leu
                     75                  80                  85

GGC AAG CAC AG                                                      107
Gly Lys His
```

( 2 ) INFORMATION FOR SEQ ID NO:6:

( i ) SEQUENCE CHARACTERISTICS:
        ( A ) LENGTH: 35 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Leu Thr Met Gly Tyr Trp Pro Thr Tyr Thr Pro Met Glu Val His Leu
 1               5                  10                  15

Thr Pro Glu Met Ile Lys Leu Gln Glu Val Phe Lys Ala Phe Tyr Leu
                20                  25                  30

Gly Lys His
       35
```

( 2 ) INFORMATION FOR SEQ ID NO:7:

( i ) SEQUENCE CHARACTERISTICS:
        ( A ) LENGTH: 114 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 3..113

( x i ) SEQUENCE DESCRIPTION: SEQ ID NO:7:

```
TG TTT GTT CAC CCA AAT TGT AAA TAT GAT GCA AAG TGT ACT AAA CCA       47
   Phe Val His Pro Asn Cys Lys Tyr Asp Ala Lys Cys Thr Lys Pro
                         40                  45                  50

GAT TGT CCC TTC ACT CAT GTG AGT AGA AGA ATT CCA GTA CTG TCT CCA      95
Asp Cys Pro Phe Thr His Val Ser Arg Arg Ile Pro Val Leu Ser Pro
                     55                  60                  65

AAA CCA GTT GCA CCA CCA G                                           114
Lys Pro Val Ala Pro Pro
```

( 2 ) INFORMATION FOR SEQ ID NO:8:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Phe Val His Pro Asn Cys Lys Tyr Asp Ala Lys Cys Thr Lys Pro Asp
 1               5                  10                  15

Cys Pro Phe Thr His Val Ser Arg Arg Ile Pro Val Leu Ser Pro Lys
            20                  25                  30

Pro Val Ala Pro Pro
            35
```

( 2 ) INFORMATION FOR SEQ ID NO:9:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

TTTTTTTTT TCC                              13

( 2 ) INFORMATION FOR SEQ ID NO:10:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

TTTTTTTTT TAC                              13

( 2 ) INFORMATION FOR SEQ ID NO:11:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

CAATCGCCGT                                10

( 2 ) INFORMATION FOR SEQ ID NO:12:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

TCGGCGATAG                                10

( 2 ) INFORMATION FOR SEQ ID NO:13:

( i ) SEQUENCE CHARACTERISTICS:
        ( A ) LENGTH: 10 base pairs

```
            ( B ) TYPE: nucleic acid
            ( C ) STRANDEDNESS: single
            ( D ) TOPOLOGY: linear ( x i ) SEQUENCE DESCRIPTION: SEQ ID NO:13:

CAGCACCCAC                                                                  10

( 2 ) INFORMATION FOR SEQ ID NO:14:

( i ) SEQUENCE CHARACTERISTICS:
            ( A ) LENGTH: 10 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:14:

AGCCAGCGAA                                                                  10
```

TARGETS FOR BREAST CANCER DIAGNOSIS AND TREATMENT

REFERENCE TO GOVERNMENT GRANT

This invention was made in part during work supported by a grant from the National Cancer Institute (P01-CA44768). The Government has certain rights in the invention.

FIELD OF THE INVENTION

The present invention relates generally to the field of human genetics. Morespecifically, it relates to the identification of novel genes associated with overabundance of RNA in human cancer, particularly breast cancer. It pertains especially to those genes and the products thereof which may be important in diagnosis and treatment.

BACKGROUND OF THE INVENTION

One of the most pressing health issues today is breast cancer. In the industrial world, about one woman in every nine can expect to develop breast cancer in her lifetime. In the United States, it is the most common cancer amongst women, with an annual incidence of about 175,000 new cases and nearly 50,000 deaths.

Despite an ongoing improvement in our understanding of the disease, breast cancer has remained resistant to medical intervention. Most clinical initiatives are focused on early diagnosis, followed by conventional forms of intervention, particularly surgery and chemotherapy. Such interventions are of limited success, particularly in patients where the tumor has undergone metastasis. There is a pressing need to improve the arsenal of therapies available to provide more precise and more effective treatment in a less invasive way.

A promising area for the development of new modalities has emerged from recent understanding of the genetics of cancer. Alteration of gene expression is intimately related to the uncontrolled growth and de-differentiation that are hallmarks of the disease. There are two classes of alterations that take place (Bishop). The first type is the decreased expression of recessive genes, known as tumor suppressor genes, that apparently act to prevent malignant growth. The second type is the increased expression of dominant genes, such as oncogenes, that act to promote malignant growth, or to provide some other phenotype critical for malignancy. Thus, alteration in the expression of either type of gene is a potential diagnostic indicator. Furthermore, a treatment strategy might seek to reinstate the expression of suppressor genes, or reduce the expression of dominant genes. The latter strategy is a focus of the present invention.

The most frequently studied mechanism for gene overexpression in cancer cells is generally referred to in the literature as amplification. This is a process whereby the gene is duplicated within the chromosomes of the ancestral cell into multiple copies. The process involves unscheduled replications of the region of the chromosome comprising the gene, followed by recombination of the replicated segments back into the chromosome (Alitalo et al.). As a result, 50 or more copies of the gene may be produced. The duplicated region is sometimes referred to as an "amplicon". The level of expression of the gene (that is, the amount of messenger RNA produced) escalates in the transformed cell in the same proportion as the number of copies of the gene that are made (Alitalo et al.).

Several human oncogenes have been described, some of which are duplicated in a significant proportion of breast tumors. A prototype is the erbB2 gene (also known as HER-2/neu), which encodes a 185 kDa membrane growth factor receptor homologous to the epidermal growth factor receptor. erbB2 is duplicated in 61 of 283 tumors (22%) tested in a recent survey (Adnane et al.). Other oncogenes duplicated in breast cancer are the bek gene, duplicated in 34 out of 286 (12%); the flg gene, duplicated in 37 out of 297 (12%), the myc gene, duplicated in 43 out of 275 (16%) (Adnane et al.).

Work with other oncogenes, particularly those described for neuroblastoma, suggested that gene duplication of the proto-oncogene was an event involved in the more malignant forms of cancer, and could act as a predictor of clinical outcome (reviewed by Schwab et al. and Alitalo et al.). In breast cancer, duplication of the erbB2 gene has been reported as correlating both with reoccurrence of the disease and decreased survival times (Slamon et al.). There is some evidence that erbB2 helps identify tumors that are responsive to adjuvant chemotherapy with cyclophosphamide, doxorubicin, and fluorouracil (Muss et al.).

It is clear that only a proportion of the genes that can undergo gene duplication in breast cancer have been identified. First, chromosome abnormalities, such as double minute (DM) chromosomes and homogeneously stained regions (HSRs), are abundant in cancer cells. HSRs are chromosomal regions that appear in karyotype analysis with intermediate density Giemsa staining throughout their length, rather than with the normal pattern of alternating dark and light bands. They correspond to multiple gene repeats. HSRs are particularly abundant in breast cancers, showing up in 60–65% of tumors surveyed (Dutrillaux et al., Zafrani et al.). When such regions are checked by in situ hybridization with probes for any of 16 known human oncogenes, including erbB2 and myc, only a proportion of tumors show any hybridization to HSR regions. Furthermore, only a proportion of the HSRs within each karyotype are implicated.

Second, comparative genomic hybridization (CGH) has revealed the presence of copy number increases in tumors, even in chromosomal regions outside of HSRs. CGH is a new method in which whole chromosome spreads are stained simultaneously with DNA fragments from normal cells and from cancer cells, using two different fluorochromes. The images are computer-processed for the fluorescence ratio, revealing chromosomal regions that have undergone amplification or deletion in the cancer cells (Kallioniemi et al. 1992). This method was recently applied to 15 breast cancer cell lines (Kallioniemi et al. 1994). DNA sequence copy number increases were detected in all 23 chromosome pairs.

Cloning the other genes that undergo duplication in cancer is a formidable challenge. The known human oncogenes have generally been identified by hybridizing with probes for other known growth-promoting genes, particularly known oncogenes in other species. For example, the erbB2 gene was identified using a probe from a chemically induced rat neuroglioblastoma (Slamon et al.). Genes with novel sequences and functions will evade this type of search. The CGH method is able to indicate the approximate chromosomal location of duplicated genes, but leaves an extensive amount of experimentation to identify the particular gene involved.

Furthermore, a gene can be overexpressed so as to support tumor malignancy without being duplicated within the chromosome. Increased expression can come about through a higher level of transcription of the gene; for example, by up-regulation of the promoter or substitution with an alternative promoter. It can also occur if the transcription product is able to persist longer in the cell; for example, by increasing the resistance to cytoplasmic RNase or by reducing the level of such cytoplasmic enzymes. Two examples are the epidermal growth factor receptor, overexpressed in 45% of breast cancer tumors (Klijn et al.), and the IGF-1 receptor, overexpressed in 50–93% of breast cancer tumors (Berns et al.). In almost all cases, the overexpression of each of these receptors is by a mechanism other than gene duplication.

The traditional way of examining overexpression at the messenger RNA level is by subtractive hybridization. It involves producing positive and negative cDNA strands from two RNA preparations, and looking for cDNA which is not completely hybridized by the opposing preparation. This is a laborious procedure which has distinct limitations in cancer research. In particular, since each subtraction involves cDNA from only two cell populations at a time, it is sensitive to individual phenotypic variation.

Alternatively, expression can be examined by differential display (Liang et al. 1992). In this technique, cDNA is prepared from only a subpopulation of each RNA preparation, and expanded via the polymerase chain reaction using primers of particular specificity. Similar subpopulations are compared across several RNA preparations by gel autoradiography for expression differences. In order to survey the RNA preparations entirely, the assay must be repeated with a comprehensive set of PCR primers. The method has recently been applied to breast cancer cell lines, and highlights a number of expression differences (Liang et al. 1994). By excising the corresponding region of the separating gel, it is possible to recover and sequence the cDNA.

Despite the advancement provided by differential display, problems remain in terms of applying it in the search for new cancer genes. Because this is a test for RNA levels, any phenotypic difference between cell lines will constitute part of the recovered set. This leads to a number of "false positive" identifications. We have found that cDNA for mitochondrial genes constitute a large majority of the differentially expressed bands, and it consumes substantial resources to recover the sample and obtain a partial sequence in order to eliminate them. A number of adjustments are made to gene expression levels when a cell undergoes malignant transformation or cultured in vitro. Most of these adjustments are secondary, and not part of the transformation process. Thus, even when a novel sequence is obtained from the differential display, it is far from certain that the corresponding gene is at the root of the disease process.

SUMMARY OF THE INVENTION

It is an objective of this invention to provide isolated polynucleotides, polypeptides, and antibodies derived from four novel genes which are associated with breast cancer. These genes show RNA overabundance in a majority of cancer cell lines tested. A majority of the cells showing RNA overabundance also have duplication of the corresponding gene. Another object of this invention is to provide materials and methods based on these polynucleotides, polypeptides, and antibodies for use in the diagnosis and treatment of cancer, particularly breast cancer. A further object of this invention is to provide a new strategy for searching for cancer genes likely to be important in cancer diagnosis and therapy, including those herein described.

This invention provides an isolated polynucleotide comprising a linear sequence essentially identical to a sequence contained within CH1-9a11-2, CH8-2a13-1, CH13-2a12-1, or CH14-2a16-1. These designations refer to both strands of the cDNA and fragments thereof; and to the respective corresponding messenger RNA, including splice variants, allelic variants, and fragments of any of these forms. Preferably, a sequence of at least 10 nucleotides is essentially identical between the polynucleotide of the invention and the polynucleotide of the designation; more preferably, a sequence of at least about 15 nucleotides is essentially identical; more preferably, a sequence of at least about 40 nucleotides is essentially identical; even more preferably, a sequence of at least about 70 nucleotides is essentially identical; still more preferably, a sequence of about 100 nucleotides or more is essentially identical.

Accordingly, one embodiment of this invention is an isolated polynucleotide comprising a linear sequence contained in a polynucleotide selected from the group consisting of CH1-9a11-2, CH8-2a13-1, CH13-2a12-1, and CH14-2a16-1. Preferably, said RNA is overabundant in a proportion of breast cancer cells. Preferably, the RNA is overabundant in at least about 20% of a representative panel of breast cancer cell lines; more preferably, it is overabundant in at least about 40% of the panel; even more preferably, it is overabundant in at least 60% or more of the panel. Another embodiment of this invention is the aforementioned isolated polynucleotide, comprising a linear sequence of at least 40 nucleotides essentially identical to a sequence contained in the polynucleotide selected from said group. A further embodiment of this invention is an isolated polynucleotide comprising a linear sequence essentially identical to a sequence selected from the group consisting of SEQ. ID NO:1, SEQ. ID NO:3, SEQ. ID NO:5, and SEQ. ID NO:7. These embodiments include an isolated polynucleotide which is a DNA polynucleotide, an RNA polynucleotide, a polynucleotide probe, or a polynucleotide primer.

This invention also provides an isolated polypeptide comprising a sequence of amino acids essentially identical to the polypeptide encoded by any of the polynucleotides of this invention. Preferably, a sequence of at least about 5 amino acids is essentially identical between the polypeptide of this invention and that encoded by the polynucleotide; more preferably, a sequence of at least about 10 amino acids is essentially identical; more preferably, a sequence of at least 15 amino acids is essentially identical; even more preferably, a sequence of at least 20 amino acids is essentially identical; still more preferably, a sequence of about 30 amino acids or more is essentially identical.

Accordingly, an embodiment of this invention is an isolated polypeptide comprising a linear sequence of at least 5 amino acid residues identical to a sequence encoded by a polynucleotide selected from the group consisting of CH1-9a11-2, CH8-2a13-1, CH13-2a12-1, and CH14-2a16-1. Another embodiment of this invention is the aforementioned polypeptide, comprising a linear sequence of at least 15 amino acids essentially identical to a sequence encoded by said polynucleotide. Another embodiment of this invention is the aforementioned polypeptide, comprising a linear sequence essentially identical to a sequence selected from the group consisting of SEQ. ID NO:2, SEQ. ID NO:4, SEQ. ID NO:6 and SEQ. ID NO:8.

A further embodiment of this invention is an antibody specific for a polypeptide embodied in this invention. This encompasses both monoclonal and polyclonal antibodies.

A further embodiment of this invention is a method of using the polynucleotides of this invention for detecting or measuring gene duplication in cancerous cells, particularly breast cancer cells, comprising the steps of reacting DNA contained in a clinical sample with a reagent comprising the polynucleotide, said clinical sample having been obtained from an individual suspected of having cancerous cells; and comparing the amount of complexes formed between the reagent and the DNA in the clinical sample with the amount of complexes formed between the reagent and DNA in a control sample.

A further embodiment of this invention is a method of using the polynucleotides of this invention for detecting or measuring overabundance of RNA in cancerous cells, particularly breast cancer cells, comprising the steps of reacting RNA contained in a clinical sample with a reagent comprising the polynucleotide, said clinical sample having been obtained from an individual suspected of having cancerous cells; and comparing the amount of complexes formed between the reagent and the RNA in the clinical sample with the amount of complexes formed between the reagent and RNA in a control sample.

Another embodiment of this invention is a diagnostic kit for detecting or measuring gene duplication or RNA overabundance in cells contained in an individual as manifest in a clinical sample, comprising a reagent and a buffer in suitable packaging, wherein the reagent comprises the polynucleotide of a preceding embodiment.

Another embodiment of this invention is a method of using a polypeptide of this invention for detecting or measuring specific antibodies in a clinical sample, comprising the steps of reacting antibodies contained in the clinical sample with a reagent comprising the polypeptide, said clinical sample having been obtained from an individual suspected of having cancerous cells, particularly breast cancer cells; and comparing the amount of complexes formed between the reagent and the antibodies in the clinical sample with the amount of complexes formed between the reagent and antibodies in a control sample. Still another embodiment of this invention is a diagnostic kit for detecting or measuring specific antibodies present in a clinical sample, comprising a reagent and a buffer in suitable packaging, wherein the reagent comprises the polypeptide of a preceding embodiment.

Another embodiment of this invention is a method of using an antibody of this invention for detecting or measuring altered protein expression in a clinical sample, comprising the steps of reacting a polypeptide contained in the clinical sample with a reagent comprising the antibody, said clinical sample having been obtained from an individual suspected of having cancerous cells, particularly breast cancer cells; and comparing the amount of complexes formed between the reagent and the polypeptide in the clinical sample with the amount of complexes formed between the reagent and a polypeptide in a control sample. Still another embodiment of this invention is a diagnostic kit for detecting or measuring a polypeptide present in a clinical sample, comprising a reagent and a buffer in suitable packaging, wherein the reagent comprises the antibody of a previous embodiment.

Yet another embodiment of this invention is a host cell transfected by a polynucleotide of this invention. A further embodiment of this invention is a method for using a polynucleotide for screening a pharmaceutical candidate, comprising the steps of separating progeny of the transfected host cell into a first group and a second group; treating the first group of cells with the pharmaceutical candidate; not treating the second group of cells with the pharmaceutical candidate; and comparing the phenotype of the treated cells with that of the untreated cells.

This invention also embodies a pharmaceutical preparation for use in cancer therapy, comprising the polynucleotide embodied by this invention, said preparation being capable of reducing the pathology of cancerous cells, particularly breast cancer cells. This invention further embodies a pharmaceutical preparation for use in cancer therapy comprising an antibody embodied by this invention, said preparation being capable of reducing the pathology of cancerous cells, particularly breast cancer cells. Further embodiments of this invention are methods for treating an individual bearing cancerous cells, particularly breast cancer cells, comprising administering any of the aforementioned pharmaceutical preparations.

Still another embodiment of this invention is a pharmaceutical preparation comprising a polypeptide embodied by this invention in an immunogenic form and a pharmaceutically compatible excipient. This includes a pharmaceutical preparation which constitutes an active vaccine. A further embodiment is a method for treatment of cancer, particularly breast cancer, either prophylactically or after cancerous cells are present in the individual being treated, comprising administration of the aforementioned pharmaceutical preparation.

Yet another embodiment of this invention is a method for obtaining cDNA corresponding to a gene associated with cancer, including breast cancer, comprising the steps of: a) supplying an RNA preparation from uncultured control cells; b) supplying RNA preparations from at least two different cancer cells; c) displaying cDNA corresponding to the RNA preparations of step a) and step b) such that different cDNA corresponding to different RNA in each preparation are displayed separately; d) selecting cDNA corresponding to RNA that is present in greater abundance in the cancer cells of step b) relative to the control cells of step a); e) supplying a digested DNA preparation from control cells; f) supplying digested DNA preparations from at least two different cancer cells; g) hybridizing the cDNA of step d) with the digested DNA preparations of step e) and step f); and h) further selecting cDNA from the cDNA of step d) corresponding to genes that are duplicated in the cancer cells of step f) relative to the control cells of step e).

DETAILED DESCRIPTION OF THE INVENTION

Figure 1:
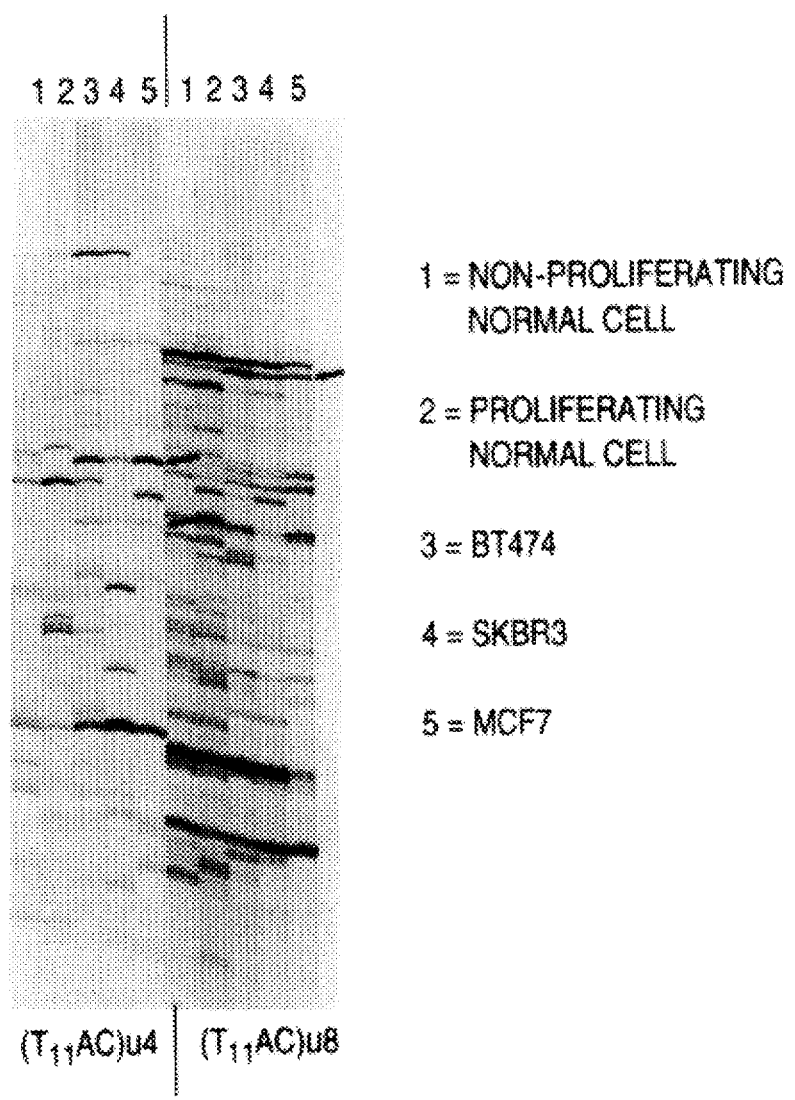
FIG. 1 is a half-tone reproduction of an autoradiogram of a differential display experiment, in which radiolabeled cDNA corresponding to a subset of total messenger RNA in different cells are compared. This is used to select cDNA corresponding to particular RNA that are overabundant in breast cancer.

We have discovered and characterized four novel genes associated with breast cancer. The cDNA of these genes, and their sequences as disclosed below, provide the basis of a series of reagents that can be used in diagnosis and therapy.

Using a panel of about 15 cancer cell lines, each of the four genes was found to be duplicated in 40–60% of the cells tested. We were surprised to find that each of the four genes was duplicated in at least one cell line where studies using comparative genomic hybridization had not revealed any amplification of the corresponding chromosomal region.

Levels of expression at the mRNA level were tested in a similar panel for two of these four genes. In addition to those cell lines showing gene duplication, 17 to 37% of the lines showed RNA overabundance without gene duplication, indicating that the malignant cells had used some mechanism other than gene duplication to promote the abundance of RNA corresponding to these genes.

Different tumors bear different genotypes and phenotypes, even when derived from the same tissue. Gene therapy in cancer is more likely to be effective if it is aimed at genes that are involved in supporting the malignancy of the cancer. This invention discloses genes that achieve RNA overabundance by several mechanisms, because they are more likely to be directly involved in the pathogenic process, and therefore suitable targets for pharmacological manipulation.

Features of the four novel genes, the respective mRNA, and the cDNA used to find them are provided in Table 1.

TABLE 1

| Characteristics of 4 Novel Breast Cancer Genes | | | |
|---|---|---|---|
| Chromosomal Location | Designation | mRNA Observed | cDNA Fragment Cloned |
| 1 | CH1-9a11-2 | 5.5 kb, 4.5 kb | 2.0 kb |
| 8 | CH8-2a13-1 | 4.2 kb | 4.0 kb |
| 13 | CH13-2a12-1 | 2.5 kb, 2.3 kb | 1.5 kb |
| 14 | CH14-2a16-1 | 3.8 kb, 3 kb | 1.4 kb |

The term "polynucleotide" refers to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The term polynucleotide, as used herein, refers interchangeably to double-and single-stranded molecules. Unless otherwise specified or required, any embodiment of the invention described herein that is a polynucleotide encompasses both the double-stranded form, and each of two complementary single-stranded forms known or predicted to make up the double-stranded form.

In the context of polynucleotides, a "linear sequence" or a "sequence" is an order of nucleotides in a polynucleotide in a 5' to 3' direction in which residues that neighbor each other in the sequence are contiguous in the primary structure of the polynucleotide. A "partial sequence" is a linear sequence of part of a polynucleotide which is known to comprise additional residues in one or both directions.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR, or the enzymatic cleavage of a polynucleotide by a ribozyme.

Hybridization reactions can be performed under conditions of different "stringency". Relevant conditions include temperature, ionic strength, time of incubation, the presence of additional solutes in the reaction mixture such as formamide, and the washing procedure. Higher stringency conditions are those conditions, such as higher temperature and lower sodium ion concentration, which require higher minimum complementarity between hybridizing elements for a stable hybridization complex to form. Conditions that increase the stringency of a hybridization reaction are widely known and published in the art: see, for example, "Molecular Cloning: A Laboratory Manual", Second Edition (Sambrook, Fritsch & Maniatis, 1989).

When hybridization occurs in an antiparallel configuration between two single-stranded polynucleotides, those polynucleotides are described as "complementary". A double-stranded polynucleotide can be "complementary" to another polynucleotide, if hybridization can occur between one of the strands of the first polynucleotide and the second. Complementarity (the degree that one polynucleotide is complementary with another) is quantifiable in terms of the proportion of bases in opposing strands that are expected to form hydrogen bonding with each other, according to generally accepted base-pairing rules.

A linear sequence of nucleotides is "identical" to another linear sequence, if the order of nucleotides in each sequence is the same, and occurs without substitution, deletion, or material substitution. It is understood that purine and pyrimidine nitrogenous bases with similar structures can be functionally equivalent in terms of Watson-Crick base-pairing; and the inter-substitution of like nitrogenous bases, particularly uracil and thymine, or the modification of nitrogenous bases, such as by methylation, does not constitute a material substitution. An RNA and a DNA polynucleotide have identical sequences when the sequence for the RNA reflects the order of nitrogenous bases in the polyribonucleotides, the sequence for the DNA reflects the order of nitrogenous bases in the polydeoxyribonucleotides, and the two sequences satisfy the other requirements of this definition. Where one or both of the polynucleotides being compared is double-stranded, the sequences are identical if one strand of the first polynucleotide is identical with one strand of the second polynucleotide.

A linear sequence of nucleotides is "essentially identical" to another linear sequence, if both sequences are capable of hybridizing to form a duplex with the same complementary polynucleotide. Sequences that hybridize under conditions of greater stringency are more preferred. It is understood that hybridization reactions can accommodate insertions, deletions, and substitutions in the nucleotide sequence.

Thus, linear sequences of nucleotides can be essentially identical even if some of the nucleotide residues do not precisely correspond or align. In general, essentially identical sequences of about 40 nucleotides in length will hybridize at about 30° C. in 10× SSC (0.15M NaCl, 15 mM citrate buffer); preferably, they will hybridize at about 40° C. in 6× SSC; more preferably, they will hybridize at about 50° C. in 6× SSC; even more preferably, they will hybridize at about 60° C. in 6× SSC, or at about 40° C. in 0.5× SSC, or at about 30° C. in 6× SSC containing 50% formamide; still more preferably, they will hybridize at 40° C. or higher in 2× SSC or lower in the presence of 50% or more formamide. It is understood that the rigor of the test is partly a function of the length of the polynucleotide; hence shorter polynucleotides with the same homology should, be tested under lower stringency and longer polynucleotides should be tested under higher stringency, adjusting the conditions accordingly. The relationship between hybridization stringency, degree of sequence identity, and polynucleotide length is known in the art and can be calculated by standard formulae; see, e.g., Meinkoth et al. Sequences that correspond or align more closely to the invention disclosed herein are comparably more preferred. Generally, essentially identical sequences are at least about 50% identical with each other, after alignment of the homologous regions. Preferably, the sequences are at least about 60% identical; more preferably, they are at least about 70% identical; more preferably, they are at least about 80% identical; more preferably, the sequences are at least about 90% identical; even more preferably, they are at least 95% identical; still more preferably, the sequences are 100% identical.

In determining whether polynucleotide sequences are essentially identical, a sequence that preserves the functionality of the polynucleotide with which it is being compared is particularly preferred. Functionality may be established by different criteria, such as ability to hybridize with a target polynucleotide, and whether the polynucleotide encodes an identical or essentially identical polypeptides. Thus, nucleotide substitutions which cause a non-conservative substitution in the encoded polypeptide are preferred over nucleotide substitutions that create a stop codon; nucleotide substitutions that cause a conservative substitution in the encoded polypeptide are more preferred, and identical nucleotide sequences are even more preferred. Insertions or deletions in the polynucleotide that result in insertions or deletions in the polypeptide are preferred over those that result in the downstream coding region being rendered out of phase. The relative importance of hybridization properties and the polypeptide encoded by a polynucleotide depends on the application of the invention.

A "reagent" polynucleotide, polypeptide, or antibody, is a substance provided for a reaction, the substance having some known and desirable parameters for the reaction. A reaction mixture may also contain a "target", such as a polynucleotide, antibody, or polypeptide that the reagent is capable of reacting with. For example, in some types of diagnostic tests, the amount of the target in a sample is determined by adding a reagent, allowing the reagent and target to react, and measuring the amount of reaction product. In the context of clinical management, a "target" may also be a cell, collection of cells, tissue, or organ that is the object of an administered substance, such as a pharmaceutical compound.

"cDNA" or "complementary DNA" is a single- or double-stranded DNA polynucleotide in which one strand is complementary to a messenger RNA. "Full-length cDNA" is cDNA comprised of a strand which is complementary to an entire messenger RNA molecule. A "cDNA fragment" as used herein generally represents a sub-region of the full-length form, but the entire full-length cDNA may also be included. Unless explicitly specified, the term cDNA encompasses both the full-length form and the fragment form.

Different polynucleotides are said to "correspond" to each other if one is ultimately derived from another. For example, messenger RNA corresponds to the gene from which it is transcribed. cDNA corresponds to the RNA from which it has been produced, such as by a reverse transcription reaction, or by chemical synthesis of a DNA based upon knowledge of the RNA sequence. cDNA also corresponds to the gene that encodes the RNA. Polynucleotides may be said to correspond even when one of the pair is derived from only a portion of the other.

A "probe" when used in the context of polynucleotide manipulation refers to a polynucleotide which is provided as a reagent to detect a target potentially present in a sample of interest by hybridizing with the target. Usually, a probe will comprise a label or a means by which a label can be attached, either before or subsequent to the hybridization reaction. Suitable labels include, but are not limited to radioisotopes, fluorochromes, chemiluminescent compounds, dyes, and enzymes.

A "primer" is a short polynucleotide, generally with a free 3' —OH group, that binds to a target potentially present in a sample of interest by hybridizing with the target, and thereafter promoting polymerization of a polynucleotide complementary to the target. A "polymerase chain reaction" ("PCR") is a reaction in which replicate copies are made of a target polynucleotide using one or more primers, and a catalyst of polymerization, such as a reverse transcriptase or a DNA polymerase, and particularly a thermally stable polymerase enzyme. Methods for PCR are taught in U.S. Pat. Nos. 4,683,195 (Mullis) and 4,683,202 (Mullis et al.). All processes of producing replicate copies of the same polynucleotide, such as PCR or gene cloning, are collectively referred to herein as "replication."

An "operon" is a genetic region comprising a gene encoding a protein and functionally related 5' and 3' flanking regions. Elements within an operon include but are not limited to promoter regions, enhancer regions, repressor binding regions, transcription initiation sites, ribosome binding sites, translation initiation sites, protein encoding regions, introns and exons, and termination sites for transcription and translation. A "promoter" is a DNA region capable under certain conditions of binding RNA polymerase and initiating transcription of a coding region located downstream (in the 3' direction) from the promoter. "Operably linked" refers to a juxtaposition of genetic elements, wherein the elements are in a relationship permitting them to operate in the expected manner. For instance, a promoter is operably linked to a coding region if the promoter helps initiate transcription of the coding sequence. There may be intervening residues between the promoter and coding region so long as this functional relationship is maintained.

"Gene duplication" is a term used herein to describe the process whereby an increased number of copies of a particular gene or a fragment thereof is present in a particular cell or cell line. "Gene amplification" generally is synonymous with gene duplication.

"Expression" is defined alternately in the scientific literature either as the transcription of a gene into an RNA polynucleotide, or as the transcription and subsequent translation into a polypeptide. As used herein, "expression" or "gene expression" refers primarily to the production of the RNA. Thus, "overexpression" reflects the presence of more RNA (as a proportion of total RNA) from a particular gene in a cell being described, such as a cancerous cell, in relation to that of the cell it is being compared with, such as a non-cancerous cell. The protein product of the gene may or may not be produced in normal or abnormal amounts.

"Abundance" of RNA refers to the amount of a particular RNA present in a particular cell type. Thus, "RNA overabundance" or "overabundance of RNA" describes RNA that is present in greater proportion of total RNA in the cell type being described, compared with the same RNA as a proportion of the total RNA in a control cell. A number of mechanisms may contribute to RNA overabundance in a particular cell type: for example, gene duplication, increased level of transcription of the gene, increased persistence of the RNA within the cell after it is produced, or any combination of these.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component.

In the context of polypeptides, a "linear sequence" or a "sequence" is an order of amino acids in a polypeptide in an N-terminal to C-terminal direction in which residues that neighbor each other in the sequence are contiguous in the primary structure of the polypeptide. A "partial sequence" is a linear sequence of part of a polypeptide which is known to comprise additional residues in one or both directions.

A linear sequence of amino acids is "essentially identical" to another sequence if the two sequences have a substantial degree of sequence identity. It is understood that the folding and the biological function of proteins can accommodate insertions, deletions, and substitutions in the amino acid sequence. Thus, linear sequences of amino acids can be essentially identical even if some of the residues do not precisely correspond or align. Sequences that correspond or align more closely to the invention disclosed herein are more preferred. It is also understood that some amino acid substitutions are more easily tolerated. For example, substitution of an amino acid with hydrophobic side chains, aromatic side chains, polar side chains, side chains with a positive or negative charge, or side chains comprising two or fewer carbon atoms, by another amino acid with a side chain of like properties can occur without disturbing the essential identity of the two sequences. Methods for determining homologous regions and scoring the degree of homology are well known in the art; see for example Altschul et al. and Henikoff et al. Well-tolerated sequence differences are referred to as "conservative substitutions". Thus, sequences with conservative substitutions are preferred over those with other substitutions in the same positions; sequences with identical residues at the same positions are still more preferred. In general, amino acid sequences that are essentially identical are at least about 15% identical, and comprise at least about another 15% which are either identical or are conservative substitutions, after alignment of homologous regions. More preferably, essentially identical sequences comprise at least about 50% identical residues or conservative substitutions; more preferably, they comprise at least about 70% identical residues or conservative substitutions; more preferably, they comprise at least about 80% identical residues or conservative substitutions; more preferably, they comprise at least about 90% identical residues or conservative substitutions; more preferably, they comprise at least about 95% identical residues or conservative substitutions; even more preferably, they contain 100% identical residues.

In determining whether polypeptide sequences are essentially identical, a sequence that preserves the functionality of the polypeptide with which it is being compared is particularly preferred. Functionality may be established by different parameters, such as enzymatic activity, the binding rate or affinity in a receptor-ligand interaction, the binding affinity with an antibody, and X-ray crystallographic structure.

An "antibody" (interchangeably used in plural form) is an immunoglobulin molecule capable of specific binding to a target, such as a polypeptide, through at least one antigen recognition site, located in the variable region of the immunoglobulin molecule. As used herein, the term encompasses not only intact antibodies, but also fragments thereof, mutants thereof, fusion proteins, humanized antibodies, and any other modified configuration of the immunoglobulin molecule that comprises an antigen recognition site of the required specificity.

The term "antigen" refers to the target molecule that is specifically bound by an antibody through its antigen recognition site. The antigen may, but need not be chemically related to the immunogen that stimulated production of the antibody. The antigen may be polyvalent, or it may be a monovalent hapten. Examples of kinds of antigens that can be recognized by antibodies include polypeptides, polynucleotides, other antibody molecules, oligosaccharides, complex lipids, drugs, and chemicals. An "immunogen" is an antigen capable of stimulating production of an antibody when injected into a suitable host, usually a mammal. Compounds may be rendered immunogenic by many techniques known in the art, including crosslinking or conjugating with a carrier to increase valency, mixing with a mitogen to increase the immune response, and combining with an adjuvant to enhance presentation.

An "active vaccine" is a pharmaceutical preparation for human or animal use, which is used with the intention of eliciting a specific immune response. The immune response may be either humoral or cellular, systemic or secretory. The immune response may be desired for experimental purposes, for the treatment of a particular condition, for the elimination of a particular substance, or for prophylaxis against a particular condition or substance.

An "isolated" polynucleotide, polypeptide, protein, antibody, or other substance refers to a preparation of the substance devoid of at least some of the other components that may also be present where the substance or a similar substance naturally occurs or is initially obtained from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this invention are increasingly more preferred. Thus, for example, a 2-fold enrichment is preferred, 10-fold enrichment is more preferred, 100-fold enrichment is more preferred, 1000-fold enrichment is even more preferred. A substance can also be provided in an isolated state by a process of artificial assembly, such as by chemical synthesis or recombinant expression.

A polynucleotide used in a reaction, such as a probe used in a hybridization reaction, a primer used in a PCR, or a polynucleotide present in a pharmaceutical preparation, is referred to as "specific" or "selective" if it hybridizes or reacts with the intended target more frequently, more rapidly, or with greater duration than it does with alternative substances. Similarly, an antibody is referred to as "specific" or "selective" if it binds via at least one antigen recognition site to the intended target more frequently, more rapidly, or with greater duration than it does to alternative substances. A polynucleotide or antibody is said to "selectively inhibit" or "selectively interfere with" a reaction if it inhibits or interferes with the reaction between particular substrates to a greater degree or for a greater duration than it does with the reaction between alternative substrates. An antibody is capable of "specifically delivering" a substance if it conveys or retains that substance near a particular cell type more frequently than to other cell types.

The "effector component" of a pharmaceutical preparation is a component which modifies target cells by altering their function in a desirable way when administered to a subject bearing the cells. Some advanced pharmaceutical preparations also have a "targeting component", such as an antibody, which helps deliver the effector component more efficaciously to the target site. Depending on the desired action, the effector component may have any one of a number of modes of action. For example, it may restore or enhance a normal function of a cell, it may eliminate or suppress an abnormal function of a cell, or it may alter a cell's phenotype. Alternatively, it may kill or render dormant a cell with pathological features, such as a cancer cell. Examples of effector components are provided in a later section.

A "pharmaceutical candidate" or "drug candidate" is a compound believed to have therapeutic potential, that is to be tested for efficacy. The "screening" of a pharmaceutical candidate refers to conducting an assay that is capable of evaluating the efficacy and/or specificity of the candidate. In this context, "efficacy" refers to the ability of the candidate to effect the cell or organism it is administered to in a beneficial way: for example, the limitation of the pathology of cancerous cells. A "cell line" or "cell culture" denotes higher eukaryotic cells grown or maintained in vitro. It is understood that the descendants of a cell may not be completely identical (either morphologically, genotypically, or phenotypically) to the parent cell. Cells described as "uncultured" are obtained directly from a living organism, and have been maintained for a limited amount of time away from the organism: not long enough or under conditions for the cells to undergo substantial replication.

A "host cell" is a cell which has been transformed, or is capable of being transformed, by administration of an exogenous polynucleotide.

The terms "cancerous cell" or "cancer cell", used either in the singular or plural form, refer to cells that have undergone a malignant transformation that makes them pathological to the host organism. Malignant transformation is a single- or multi-step process, which involves in part an alteration in the genetic makeup of the cell and/or the expression profile. Malignant transformation may occur either spontaneously, or via an event or combination of events such as drug or chemical treatment, radiation, fusion with other cells, viral infection, or activation or inactivation of particular genes. Malignant transformation may occur in vivo or in vitro, and can if necessary be experimentally induced.

A frequent feature of cancer cells is the tendency to grow in a manner that is uncontrollable by the host, but the pathology associated with a particular cancer cell may take another form, as outlined infra. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells.

The "pathology" caused by a cancer cell within a host is anything that compromises the well-being or normal physiology of the host. This may involve (but is not limited to) abnormal or uncontrollable growth of the cell, metastasis, release of cytokines or other secretory products at an inappropriate level, manifestation of a function inappropriate for its physiological milieu, interference with the normal function of neighboring cells, aggravation or suppression of an inflammatory or immunological response, or the harboring of undesirable chemical agents or invasive organisms.

"Treatment" of an individual or a cell is any type of intervention in an attempt to alter the natural course of the individual or cell. For example, treatment of an individual may be undertaken to decrease or limit the pathology caused by a cancer cell harbored in the individual. Treatment includes (but is not limited to) administration of a composition, such as a pharmaceutical composition, and may be performed either prophylactically, or subsequent to the initiation of a pathologic event or contact with an etiologic agent.

A "control cell" is an alternative source of cells or an alternative cell line used in an experiment for comparison purposes. Where the purpose of the experiment is to establish a base line for gene copy number or expression level, it is generally preferable to use a control cell that is not a cancer cell.

The term "cancer gene" as used herein refers to any gene which is yielding transcription or translation products at a substantially altered level or in a substantially altered form in cancerous cells compared with non-cancerous cells, and which may play a role in supporting the malignancy of the cell. It may be a normally quiescent gene that becomes activated (such as a dominant proto-oncogene), it may be a gene that becomes expressed at an abnormally high level (such as a growth factor receptor), it may be a gene that becomes mutated to produce a variant phenotype, or it may be a gene that becomes expressed at an abnormally low level (such as a tumor suppressor gene). The present invention is particularly directed towards the discovery of genes in the first two categories.

It is understood that a "clinical sample" encompasses a variety of sample types obtained from a subject and useful in an in vitro procedure, such as a diagnostic test. The definition encompasses solid tissue samples obtained as a surgical removal, a pathology specimen, or a biopsy specimen, tissue cultures or cells derived therefrom and the progeny thereof, and sections or smears prepared from any of these sources. Non-limiting examples are samples obtained from breast tissue, lymph nodes, and tumors. The definition also encompasses blood, spinal fluid, and other liquid sample of biologic origin, and may refer to either the cells or cell fragments suspended therein, or to the liquid medium and its solutes.

The term "relative amount" is used where a comparison is made between a test measurement and a control measurement. Thus, the relative amount of a reagent forming a complex in a reaction is the amount reacting with a test specimen, compared with the amount reacting with a control specimen. The control specimen may be run separately in the same assay, or it may be part of the same sample (for example, normal tissue surrounding a malignant area in a tissue section).

A "differential" result is generally obtained from an assay in which a comparison is made between the findings of two different assay samples, such as a cancerous cell line and a control cell line. Thus, for example, "differential expression" is observed when the level of expression of a particular gene is higher in one cell than another. "Differential display" refers to a display of a component, particularly RNA, from different cells to determine if there is a difference in the level of the component amongst different cells. Differential display of RNA is conducted, for example, by selective production and display of cDNA corresponding thereto. A method for performing differential display is provided in a later section.

The practice of the present invention will employ, unless otherwise indicated, conventional techniques of molecular biology, microbiology, recombinant DNA, and immunology, which are within the skill of the art. Such techniques are explained fully in the literature. See, for example, "Molecular Cloning: A Laboratory Manual", Second Edition (Sambrook, Fritsch & Maniatis, 1989), "Oligonucleotide Synthesis" (M. J. Gait, ed., 1984), "Animal Cell Culture" (R. I. Freshney, ed., 1987); the series "Methods in Enzymology" (Academic Press, Inc.); "Handbook of Experimental Immunology" (D. M. Weir & C. C. Blackwell, Eds.), "Gene Transfer Vectors for Mammalian Cells" (J. M. Miller & M. P. Calos, eds., 1987), "Current Protocols in Molecular Biology" (F. M. Ausubel et al., eds., 1987); and "Current Protocols in Immunology" (J. E. Coligan et al., eds., 1991). All patents, patent applications, articles and publications mentioned herein, both supra and infra, are hereby incorporated herein by reference.

A polynucleotide derived from or corresponding to CH1-9a11-2, CH8-2a13-1, CH13-2a12-1, or CH14-2a16-1 is any of the following: the respective cDNA fragments, the corresponding messenger RNA, including splice variants and fragments thereof, both strands of the corresponding full-length cDNA and fragments thereof, and the corresponding gene. Isolated allelic variants of any of these forms are included. This invention embodies any polynucleotide corresponding to CH1-9a11-2, CH8-2a13-1, CH13-2a12-1, or CH14-2a16-1 in an isolated form. It also embodies any such polynucleotide that has been cloned or transfected into a cell line.

The experimental method used to discover the four genes disclosed herein can be brought to bear to discover other novel genes associated with cancer. The strategy can be applied to any type of cancer, not just breast cancer. It involves sequential application of different genetic techniques.

A central part of the strategy was to screen for both DNA duplication and RNA overabundance relating to the same gene. This feature is particularly powerful in the discovery of new and potentially important cancer genes. While amplicons occur frequently in cancer, the presently available techniques indicate only the broad chromosomal region involved in the duplication event, not the specific genes involved. The present invention provides a way of detecting genes that may be present in an amplicon from a functional basis. Because an early part of the method involves detecting messenger RNA, the method avoids genes that may be duplicated in an amplicon but are quiescent (and therefore irrelevant) in the cancer cells. Furthermore, it recruits active genes from a duplicated region of the chromosome too small to be detectable by the techniques used to describe amplicons.

The strategy has the additional advantage of detecting genes which are so critical to the cancer process that they take advantage of a genetic duplication event in some cells, and find alternative mechanisms to increase the level transcription in other cells. Polynucleotides derived from such genes and the polypeptides they encode are likely to be particularly good targets for both diagnosis and treatment of cancer. In particular, genes that show RNA overabundance in a large proportion of tumors or tumor cell lines, and show DNA duplication in a substantial but somewhat smaller subset of the same cells may be particularly good candidates.

The strategy for detecting such genes comprises a number of innovations over those that have been used in previous work.

The first part of the method is based on a search for particular RNAs that are overabundant in cancer cells. The first innovation of the method is to compare RNA abundance between control cells and several different cancer cell lines of the desired type. The cDNA fragments that emerge in a greater amount in several different cancer lines, but not in control cells, are more likely to reflect genes that are important in disease progression, rather than those that have undergone secondary or coincidental activation.

The second innovation of this method is to supply as control, not messenger RNA from a cell line or culture, but from fresh tissue samples of non-malignant origin. There are two reasons for this. First, the tissue will provide the spectrum of expression that is typical to the normal cell phenotype, rather than individual differences that may become more prominent in culture. This establishes a more reliable baseline for normal expression levels. More importantly, the tissue will be devoid of the effects that in vitro culturing may have in altering or selecting particular phenotypes. For example, proto-oncogenes or growth factors may become up-regulated in culture. When cultured cells are used as the control for differential display, these up-regulated genes would be missed.

The third innovation of this method is to undertake a subselection for cDNA corresponding to genes that achieve their RNA overabundance in a substantial proportion of cancer cells by gene duplication. To accomplish this, appropriate cDNA corresponding to overabundant RNA identified in the foregoing steps are used to probe digests of cellular DNA from a panel of different cancer cells, and from normal genomic DNA. cDNA that shows evidence of higher copy numbers in a proportion of the panel are selected for further characterization. An additional advantage of this step is that cDNA corresponding to mitochondrial genes can rapidly be screened away by including a mitochondrial DNA digest as an additional sample for testing the probe. This eliminates most of the false-positive cDNA, which otherwise make up a majority of the cDNA identified.

Thus, the identification of genes yielding products that are present at abnormal levels is accomplished by a method comprised of the following steps.

To identify particular RNA that is overabundant in cancer cells, RNA is prepared from both cancerous and control cells by standard techniques. The RNA is preserved until use in such a way to minimize fragmentation. To facilitate confirmation experiments, it is useful to use RNA of a reproducible character. For this reason, it is convenient to use RNA that has been obtained from stable cancerous cell lines, although reproducibility can also be provided by preparing enough RNA so that it can be preserved in aliquots. For reasons outlined earlier, it is preferable for the control RNA to be obtained directly from normal human tissue of the same type as the cancer cells. Alternatively, the control RNA can be derived from in vitro cultures of non-malignant cells, or established cell lines derived from a non-malignant source.

Any technique that detects a relative overabundance of RNA in the cancer cells, compared with the control cells, is suitable. This would include any form of subtractive hybridization or comparative analysis. A preferred method enables more than two RNA sources to be compared at the same time, such as, for example, a differential display method, in which the samples are run in neighboring lanes in a separating gel. Whole RNA can be used. It is not required to separate out mRNA, particularly if primers are used in the comparison assay that focus on the poly-A tail characteristic of MRNA.

Because many thousands of genes are expressed in the cells of higher organisms at any one time, it is preferable to improve the legibility of the display by surveying only a subset of the RNA at a time. Methods for accomplishing this are known in the art. A preferred method is by using selective primers that initiate PCR replication for a subset of the RNA. Thus, the RNA is first reverse transcribed by standard techniques. Short primers are used for the selection, preferably chosen such that alternative primers used in a series of like assays can complete a comprehensive survey of the mRNA. For example, primers can be used for the 3' region of the mRNAs which have an oligo-dT sequence, followed by two other nucleotides (TiNM, where i ≈ 11, N ∈ {A,C,G}, and M ∈ {A,C,G,T}). Thus, 12 possible primers are required to complete the survey. A random or arbitrary primer of minimal length can then be used for replication towards what corresponds in the sequence to the 5' region of the MRNA. The optimal length for the random primer is about 10 nucleotides. The product of the PCR reaction is labeled with a radioisotope, such as $^{32}P$ or $^{35}S$. The labeled cDNA is then separated by molecular weight, such as on a polyacrylamide sequencing gel. See especially Liang et al. (1992). Improvements to the differential display method have been described: see Bauer et al., Liang et al. (1993), and Trentmann et al.

Particular mRNAs are chosen which are present as a higher proportion of the RNA in cancerous cells, compared with control cells. When using the differential display method, the cDNA corresponding to overabundant RNA will produce a band with greater proportional intensity amongst neighboring cDNA bands, compared with the proportional intensity in the control lanes. Desired cDNAs can be recovered most directly by cutting the spot in the gel corresponding to the band, and recovering the DNAs therefrom. Recovered cDNA can be replicated again for further use by any technique or combination of techniques known in the art, including PCR and cloning into a suitable carrier.

A subsequent selection step in the method is aimed at identifying genes that are duplicated in a substantial proportion of cancers. This is conducted by using the cDNA from the preceding selection to probe digests of chromosomal DNA obtained from two or more cancerous cells, such as cancer cell lines. Chromosomal DNA from non-cancerous cells that essentially reflects the germ line in terms of gene copy number is used for the control. A preferred source of control DNA in experiments for human cancer genes is placental DNA, which is readily obtainable. The DNA samples are cleaved with a suitable restriction enzyme into fragments of appropriate size. The DNA can be blotted directly onto a suitable medium, or separated on an agarose gel before blotting. The latter method is preferred, because it enables a comparison of the hybridizing chromosomal restriction fragment to determine whether the probe is binding to the same fragment in all samples. The amount of probe binding to DNA digests from each of the cancer cells is compared with the amount binding to control DNA.

Because the comparison is quantitative, it is preferable to standardize the measurement internally. One method is to administer a second probe to the same blot, probing for a second chromosomal gene unlikely to be duplicated in the cancer cells. This method is preferred, because it standardizes not only for differences in the amount of DNA provided, but also for differences in the amount transferred during blotting. This can be accomplished by using alternative labels for the two probes, or by stripping the first probe with a suitable eluant before administering the second.

To eliminate cDNA for mitochondrial genes, it is preferable to include in a parallel analysis a mitochondrial DNA preparation digested with the same restriction enzyme. Any cDNA probe that hybridizes to the appropriate mitochondrial restriction fragments can be suspected of corresponding to a mitochondrial gene.

In the initial replication of the mRNA, the random primer may bind at any location along the mRNA sequence. Thus, the copied and replicated segment may be a fragment of the full-length mRNA. Longer cDNA corresponding to a greater portion of the sequence can be obtained, if desired, by several techniques known to practitioners of ordinary skill. These include using the cDNA fragment to isolate the corresponding mRNA, or to isolate complementary DNA from a cDNA library of the same species. Preferably, the library is derived from the same tissue source, and more preferably from a cancer cell line of the same type. For example, for cDNA corresponding to human breast cancer genes, a preferred library is derived from breast cancer cell line BT474, constructed in lambda GT10.

Sequences of the cDNA can be determined by standard techniques, or by submitting the sample to commercial sequencing services. The chromosomal locations of the genes can be determined by any one of several methods known in the art, such as in situ hybridization using chromosomal smears, or panels of somatic cell hybrids of known chromosomal composition.

The cDNA obtained through the selection process outlined can then be tested against a larger panel of breast cancer cell lines and/or fresh tumor cells to determine what proportion of the cells have duplicated the gene. This can be accomplished by using the cDNA as a probe for chromosomal DNA digests, as described earlier.

The cDNA can also be used to determine what proportion of the cells have RNA overabundance. This can be accomplished by standard techniques, such as slot blots or blots of agarose gels, using whole RNA or messenger RNA from each of the cells in the panel. The blots are then probed with the cDNA using standard techniques. It is preferable to provide an internal loading and blotting control for this analysis. A preferred method is to re-probe the same blot for transcripts of a gene likely to be present in about the same evel in all cells of the same type, such as the gene for a cytoskeletal protein. Thus, a referred second probe is the cDNA for beta-actin.

Using a novel cDNA found by this selection procedure, it is anticipated that essentially all cancer cells showing gene duplication will also show RNA overabundance, but that some will show RNA overabundance without gene duplication.

cDNA selected by the strategy just outlined, particularly CH1-9a11-2, CH8-2a13-1, CH13-2a12-1, CH14-2a16-1, and polynucleotides containing portions thereof, can be replicated to provide a larger supply by any standard technique, such as PCR or gene cloning. Alternatively, the cDNA can be sequenced, and the sequence data can be used to produce a polynucleotide by artificial synthesis that is identical in sequence, or that incorporates occasional variations. Devices are commercially available that perform the synthesis reactions automatically.

Polypeptides encoded by the corresponding mRNA can be prepared by several different methods, all of which will be known to a practitioner of ordinary skill. For example, the appropriate strand of the full-length cDNA can be operably linked to a suitable promoter, and transfected into a suitable host cell. The host cell is then cultured under conditions that allow transcription and translation to occur, and the polypeptide is subsequently recovered. Another convenient method is to determine the polynucleotide sequence of the cDNA, and predict the polypeptide sequence according to the genetic code. A polypeptide can then be prepared directly, for example, by chemical synthesis, either identical to the predicted sequence, or incorporating occasional variations.

Antibodies against the polypeptide may be prepared by any method known in the art. For stimulating antibody production in an animal, it is often preferable to enhance the immunogenicity of a polypeptide by such techniques as polymerization with glutaraldehyde, or combining with an adjuvant, such as Freund's adjuvant. The immunogen is injected into a suitable experimental animal: preferably a rodent for the preparation of monoclonal antibodies; preferably a larger animal such as a rabbit or sheep for preparation of polyclonal antibodies. It is preferable to provide a second or booster injection after about 4 weeks, and begin harvesting the antibody source no less than about 1 week later.

Sera harvested from the immunized animals provide a source of polyclonal antibodies. Detailed procedures for purifying specific antibody activity from a source material are known within the art. Unwanted activity cross-reacting with other antigens, if present, can be removed, for example, by running the preparation over adsorbants made of those antigens attached to a solid phase, and collecting the unbound fraction. If desired, the specific antibody activity can be further purified by such techniques as protein A chromatography, ammonium sulfate precipitation, ion exchange chromatography, high-performance liquid chromatography and immunoaffinity chromatography on a column of the immunizing polypeptide coupled to a solid support.

Alternatively, immune cells such as splenocytes can be recovered from the immunized animals and used to prepare a monoclonal antibody-producing cell line. See, for example, Harrow & Lane (1988), U.S. Pat. No. 4,491,632 (J. R. Wands et al.), U.S. Pat. No. 4,472,500 (C. Milstein et al.), and U.S. Pat. No. 4,444,887 (M. K. Hoffman et al.)

Briefly, an antibody-producing line can be produced inter alia by cell fusion, or by transfecting antibody-producing cells with Epstein Barr Virus, or transforming with oncogenic DNA. The treated cells are cloned and cultured, and clones are selected that produce antibody of the desired specificity. Specificity testing can be performed on culture supernatants by a number of techniques, such as using the immunizing polypeptide as the detecting reagent in a standard immunoassay, or using cells expressing the polypeptide in immunohistochemistry. A supply of monoclonal antibody from the selected clones can be purified from a large volume of tissue culture supernatant, or from the ascites fluid of suitably prepared host animals injected with the clone.

Effective variations of this method include those in which the immunization with the polypeptide is performed on isolated cells. Antibody fragments and other derivatives can be prepared by methods of standard protein chemistry, such as subjecting the antibody to cleavage with a proteolytic enzyme. Genetically engineered variants of the antibody can be produced by obtaining a polynucleotide encoding the antibody, and applying the general methods of molecular biology to introduce mutations and translate the variant.

Novel CDNA sequences corresponding to genes associated with cancer are potentially useful as diagnostic aids. Similarly, polypeptides encoded by such genes, and antibodies specific for these polypeptides, are also potentially useful as diagnostic aids.

More specifically, gene duplication or overabundance of RNA in particular cells can help identify those cells as being cancerous, and thereby play a part in the initial diagnosis. For patients already diagnosed with cancer, gene duplication or overabundance of RNA can assist with clinical management and prognosis. For example, overabundance of RNA may be a useful predictor of disease survival, metastasis, susceptibility to various regimens of standard chemotherapy, the stage of the cancer, or its aggressiveness. See generally the article by Blast, U.S. Pat. No. 4,968,603 (Slamon et al.) and PCT Application WO 94/00601 (Levine et al.). All of these determinations are important in helping the clinician choose between the available treatment options.

A particularly important diagnostic application contemplated in this invention is the identification of patients suitable for gene-specific therapy, as outlined in the following section. For example, treatment directed against a particular gene or gene product is appropriate in cancers where the gene is duplicated or there is RNA overabundance. Given a particular pharmaceutical that is directed at a particular gene, a diagnostic test specific for the same gene is important in selecting patients likely to benefit from the pharmaceutical. Given a selection of such pharmaceuticals specific for different genes, diagnostic tests for each gene are important in selecting which pharmaceutical is likely to benefit a particular patient.

The polynucleotide, polypeptide, and antibodies embodied in this invention provide specific reagents that can be used in standard diagnostic procedures. The actual procedures for conducting diagnostic tests are extensively known in the art, and are routine for a practitioner of ordinary skill. See, for example, U.S. Pat. No. 4,968,603 (Slamon et al.), and PCT Applications WO 94/00601 (Levine et al.) and WO 94/17414 (K. Keyomarsi et al.). What follows is a brief non-limiting survey of some of the known procedures that can be applied.

Generally, to perform a diagnostic method of this invention, one of the compositions of this invention is provided as a reagent to detect a target in a clinical sample with which it reacts. Thus, the polynucleotide of this invention can be used as a reagent to detect a DNA or RNA target, such as might be present in a cell with duplication or RNA overabundance of the corresponding gene. The polypeptide can be used as a reagent to detect a target for which it has a specific binding site, such as an antibody molecule or (if the polypeptide is a receptor) the corresponding ligand. The antibody can be used as a reagent to detect a target it specifically recognizes, such as the polypeptide used as an immunogen to raise it.

The target is supplied by obtaining a suitable tissue sample from an individual for whom the diagnostic parameter is to be measured. Relevant test samples are those obtained from individuals suspected of containing cancerous cells, particularly breast cancer cells. Many types of samples are suitable for this purpose, including those that are obtained near the suspected tumor site by biopsy or surgical dissection, in vitro cultures of cells derived therefrom, blood, and blood components. If desired, the target may be partially purified from the sample or amplified before the assay is conducted. The reaction is performed by contacting the reagent with the sample under conditions that will allow a complex to form between the reagent and the target. The reaction may be performed in solution, or on a solid tissue sample, for example, using histology sections. The formation of the complex is detected by a number of techniques known in the art. For example, the reagent may be supplied with a label and unreacted reagent may be removed from the complex; the amount of remaining label thereby indicating the amount of complex formed. Further details and alternatives for complex detection are provided in the descriptions that follow.

To determine whether the amount of complex formed is representative of cancerous or non-cancerous cells, the assay result is compared with a similar assay conducted on a control sample. It is generally preferable to use a control sample which is from a noncancerous source, and otherwise similar in composition to the clinical sample being tested. However, any control sample may be suitable provided the relative amount of target in the control is known or can be used for comparative purposes. Where the assay is being conducted on tissue sections, suitable control cells with normal histopathology may surround the cancerous cells being tested. It is often preferable to conduct the assay on the test sample and the control sample simultaneously. However, if the amount of complex formed is quantifiable and sufficiently consistent, it is acceptable to assay the test sample and control sample on different days or in different laboratories.

A polynucleotide embodied in this invention can be used as a reagent for determining gene duplication or RNA overabundance that may be present in a clinical sample. The binding of the reagent polynucleotide to a target in a clinical sample generally relies in part on a hybridization reaction between a region of the polynucleotide reagent, and the DNA or RNA in a sample being tested.

If desired, the nucleic acid may be extracted from the sample, and may also be partially purified. To measure gene duplication, the preparation is preferably enriched for chromosomal DNA; to measure RNA overabundance, the preparation is preferably enriched for RNA. The target polynucleotide can be optionally subjected to any combination of additional treatments, including digestion with restriction endonucleases, size separation, for example by electrophoresis in agarose or polyacrylamide, and affixed to a reaction matrix, such as a blotting material.

Hybridization is allowed to occur by mixing the reagent polynucleotide with a sample suspected of containing a target polynucleotide under appropriate reaction conditions. This may be followed by washing or separation to remove unreacted reagent. Generally, both the target polynucleotide and the reagent must be at least partly equilibrated into the single-stranded form in order for complementary sequences to hybridize efficiently. Thus, it may be useful (particularly in tests for DNA) to prepare the sample by standard denaturation techniques known in the art.

The minimum complementarity between the reagent sequence and the target sequence for a complex to form depends on the conditions under which the complex-forming reaction is allowed to occur. Such conditions include temperature, ionic strength, time of incubation, the presence of additional solutes in the reaction mixture such as formamide, and washing procedure. Higher stringency conditions are those under which higher minimum complementarity is required for stable hybridization to occur. It is generally preferable in diagnostic applications to increase the specificity of the reaction, minimizing cross-reactivity of the reagent polynucleotide alternative undesired hybridization sites in the sample. Thus, it is preferable to conduct the reaction under conditions of high stringency: for example, in the presence of high temperature, low salt, formamide, a combination of these, or followed by a low-salt wash.

In order to detect the complexes formed between the reagent and the target, the reagent is generally provided with a label. Some of the labels often used in this type of assay include radioisotopes such as $^{32}P$ and $^{33}P$, chemiluminescent or fluorescent reagents such as fluorescein, and enzymes such as alkaline phosphatase that are capable of producing a colored solute or precipitant. The label may be intrinsic to the reagent, it may be attached by direct chemical linkage, or it may be connected through a series of intermediate reactive molecules, such as a biotin-avidin complex, or a series of inter-reactive polynucleotides. The label may be added to the reagent before hybridization with the target polynucleotide, or afterwards.

To improve the sensitivity of the assay, it is often desirable to increase the signal ensuing from hybridization. This can be accomplished by replicating either the target polynucleotide or the reagent polynucleotide, such as by a polymerase chain reaction. Alternatively, a combination of serially hybridizing polynucleotides or branched polynucleotides can be used in such a way that multiple label components become incorporated into each complex. See U.S. Pat. No. 5,124,246 (Urdea et al.).

An antibody embodied in this invention can also be used as a reagent in cancer diagnosis, or for determining gene duplication or RNA overabundance that may be present in a clinical sample. This relies on the fact that overabundance of RNA in affected cells is often associated with increased production of the corresponding polypeptide. Several of the genes up-regulated in cancer cells encode for cell surface receptors—for example, erbB-2, c-myc and epidermal growth factor. Alternatively, the RNA may encode a protein kept inside the cell, or it may encode a protein secreted by the cell into the surrounding milieu.

Any such protein product can be detected in solid tissue samples and cultured cells by immunohistological techniques that will be obvious to a practitioner of ordinary skill. Generally, the tissue is preserved by a combination of techniques which may include cooling, exchanging into different solvents, fixing with agents such as paraformaldehyde, or embedding in a commercially available medium such as paraffin or OCT. A section of the sample is suitably prepared and overlaid with a primary antibody specific for the protein.

The primary antibody may be provided directly with a suitable label. More frequently, the primary antibody is detected using one of a number of developing reagents which are easily produced or available commercially. Typically, these developing reagents are anti-immunoglobulin or protein A, and they typically bear labels which include, but are not limited to: fluorescent markers such as fluorescein, enzymes such as peroxidase that are capable of precipitating a suitable chemical compound, electron dense markers such as colloidal gold, or radioisotopes such as $^{125}$I. The section is then visualized using an appropriate microscopic technique, and the level of labeling is compared between the suspected cancer cell and a control cell, such as cells surrounding the tumor area or those taken from an alternative site.

The amount of protein corresponding to the cancer-associated gene may be detected in a standard quantitative immunoassay. If the protein is secreted or shed from the cell in any appreciable amount, it may be detectable in plasma or serum samples. Alternatively, the target protein may be solubilized or extracted from a solid tissue sample. Before quantitating, the protein may optionally be affixed to a solid phase, such as by a blot technique or using a capture antibody.

A number of immunoassay methods are established in the art for performing the quantitation. For example, the protein may be mixed with a pre-determined non-limiting amount of the reagent antibody specific for the protein. The reagent antibody may contain a directly attached label, such as an enzyme or a radioisotope, or a second labeled reagent may be added, such as anti-immunoglobulin or protein A. For a solid-phase assay, unreacted reagents are removed by washing. For a liquid-phase assay, unreacted reagents are removed by some other separation technique, such as filtration or chromatography. The amount of label captured in the complex is positively related to the amount of target protein present in the test sample. A variation of this technique is a competitive assay, in which the target protein competes with a labeled analog for binding sites on the specific antibody. In this case, the amount of label captured is negatively related to the amount of target protein present in a test sample. Results obtained using any such assay on a sample from a suspected cancer-bearing source are compared with those from a non-cancerous source.

A polypeptide embodied in this invention can also be used as a reagent in cancer diagnosis, or for determining gene duplication or RNA overabundance that may be present in a clinical sample. Overabundance of RNA in affected cells may result in the corresponding polypeptide being produced by the cells in an abnormal amount. On occasion, overabundance of RNA may occur concurrently with expression of the polypeptide in an unusual form. This in turn may result in stimulation of the immune response of the host to produce its own antibody molecules that are specific for the polypeptide. Thus, a number of human hybridomas have been raised from cancer patients that produce antibodies against their own tumor antigens.

To use the polypeptide in the detection of such antibodies in a subject suspected of having cancer, an immunoassay is conducted. Suitable methods are generally the same as the immunoassays outlined in the preceding paragraphs, except that the polypeptide is provided as a reagent, and the antibody is the target in the clinical sample which is to be quantified. For example, human IgG antibody molecules present in a serum sample may be captured with solid-phase protein A, and then overlaid with the labeled polypeptide reagent. The amount of antibody would then be proportional to the label attached to the solid phase. Alternatively, cells or tissue sections expressing the polypeptide may be overlaid first with the test sample containing the antibody, and then with a detecting reagent such as labeled anti-immunoglobulin. The amount of antibody would then be proportional to the label attached to the cells. The amount of antibody detected in the sample from a suspected cancerous source would be compared with the amount detected in a control sample.

These diagnostic procedures may be performed by diagnostic laboratories, experimental laboratories, practitioners, or private individuals. This invention provides diagnostic kits which can be used in these settings. The presence of cancer cells in the individual may be manifest in a clinical sample obtained from that individual as an alteration in the DNA, RNA, protein, or antibodies contained in the sample. An alteration in one of these components resulting from the presence of cancer may take the form of an increase or decrease of the level of the component, or an alteration in the form of the component, compared with that in a sample from a healthy individual. The clinical sample is optionally pretreated for enrichment of the target being tested for. The user then applies a reagent contained in the kit in order to detect the changed level or alteration in the diagnostic component.

Each kit necessarily comprises the reagent which renders the procedure specific: a reagent polynucleotide, used for detecting target DNA or RNA; a reagent antibody, used for detecting target protein; or a reagent polypeptide, used for detecting target antibody that may be present in a sample to be analyzed. The reagent is supplied in a solid form or liquid buffer that is suitable for inventory storage, and later for exchange or addition into the reaction medium when the test is performed. Suitable packaging is provided. The kit may optionally provide additional components that are useful in the procedure. These optional components include buffers, capture reagents, developing reagents, labels, reacting surfaces, means for detection, control samples, instructions, and interpretive information.

Embodied in this invention are modes of treating subjects bearing cancer cells that have overabundance of the particular RNA described. The strategy used to obtain the cDNAs provided in this invention was deliberately focused on genes that achieve RNA overabundance by gene duplication in some cells, and by alternative mechanisms in other cells. These alternative mechanisms may include, for example, translocation or enhancement of transcription enhancing elements near the coding region of the gene, deletion of repressor binding sites, or altered production of gene regulators. Such mechanisms would result in more RNA being transcribed from the same gene. Alternatively, the same amount of RNA may be transcribed, but may persist longer in the cell, resulting in greater abundance. This could occur, for example, by reduction in the level of ribozymes or protein enzymes that degrade RNA, or in the modification of the RNA to render it more resistant to such enzymes or spontaneous degradation.

Thus, different cells make use of at least two different mechanisms to achieve a single result—the overabundance of a particular RNA. This suggests that RNA overabundance of these genes is central to the cancer process in the affected cells. Interfering with the specific gene or gene product would consequently modify the cancer process. It is an objective of this invention to provide pharmaceutical compositions that enable therapy of this kind.

One way this invention achieves this objective is through screening candidate drugs. The general screening strategy is to apply the candidate to a manifestation of a gene associated with cancer, and then determine whether the effect is beneficial and specific. For example, a composition that interferes with a polynucleotide or polypeptide corresponding any of the novel cancer-associated genes described herein has the potential to block the associated pathology when administered to a tumor of the appropriate phenotype. It is not necessary that the mechanism of interference be known; only that the interference be preferential for cancerous cells (or cells near the cancer site) but not other cells.

A preferred method of screening is to provide cells in which a polynucleotide related to a cancer gene has been transfected. See, for example, PCT application WO 93/08701.

A practitioner of ordinary skill will be well acquainted with techniques for transfecting eukaryotic cells, including the preparation of a suitable vector, such as a viral vector; conveying the vector into the cell, such as by electroporation; and selecting cells that have been transformed, such as by using a reporter or drug sensitivity element.

A cell line is chosen which has a phenotype desirable in testing, and which can be maintained well in culture. The cell line is transfected with a polynucleotide corresponding to one of the cancer-associated genes identified herein. Transfection is performed such that the polynucleotide is operably linked to a genetic controlling element that permits the correct strand of the polynucleotide to be transcribed within the cell. Successful transfection can be determined by the increased abundance of the RNA compared with an untransfected cell. It is not necessary that the cell previously be devoid of the RNA, only that the transfection result in a substantial increase in the level observed. RNA abundance in the cell is measured using the same polynucleotide, according to the hybridization assays outlined earlier.

Drug screening is performed by adding each candidate to a sample of transfected cells, and monitoring the effect. The experiment includes a parallel sample which does not receive the candidate drug. The treated and untreated cells are then compared by any suitable phenotypic criteria, including but not limited to microscopic analysis, viability testing, ability to replicate, histological examination, the level of a particular RNA or polypeptide associated with the cells, the level of enzymatic activity expressed by the cells or cell lysates, and the ability of the cells to interact with other cells or compounds. Differences between treated and untreated cells indicates effects attributable to the candidate. In a preferred method, the effect of the drug on the cell transfected with the polynucleotide is also compared with the effect on a control cell. Suitable control cells include untransfected cells of similar ancestry, cells transfected with an alternative polynucleotide, or cells transfected with the same polynucleotide in an inoperative fashion. Optimally, the drug has a greater effect on operably transfected cells than on control cells.

Desirable effects of a candidate drug include an effect on any phenotype that was conferred by transfection of the cell line with the polynucleotide from the cancer-associated gene, or an effect that could limit a pathological feature of the gene in a cancerous cell. Examples of the first type would be a drug that limits the overabundance of RNA in the transfected cell, limits production of the encoded protein, or limits the functional effect of the protein. The effect of the drug would be apparent when comparing results between treated and untreated cells. An example of the second type would be a drug that makes use of the transfected gene or a gene product to specifically poison the cell. The effect of the drug would be apparent when comparing results between operably transfected cells and control cells.

This invention also provides gene-specific pharmaceuticals in which each of the polynucleotides, polypeptides, and antibodies embodied herein as a specific active ingredient in pharmaceutical compositions. Such compositions may decrease the pathology of cancer cells on their own, or render the cancer cells more susceptible to treatment by the non-specific agents, such as classical chemotherapy or radiation.

An example of how polynucleotides embodied in this invention can be effectively used in treatment is gene therapy. See, generally, Morgan et al., Culver et al., and U.S. Pat. No. 5,399,346 (French et al.). The general principle is to introduce the polynucleotide into a cancer cell in a patient, and allow it to interfere with the expression of the corresponding gene, such as by complexing with the gene itself or with the RNA transcribed from the gene. Entry into the cell is facilitated by suitable techniques known in the art as providing the polynucleotide in the form of a suitable vector, or encapsulation of the polynucleotide in a liposome. The polynucleotide may be provided to the cancer site by an antigen-specific homing mechanism, or by direct injection.

A preferred mode of gene therapy is to provide the polynucleotide in such a way that it will replicate inside the cell, enhancing and prolonging the interference effect. Thus, the polynucleotide is operably linked to a suitable promoter, such as the natural promoter of the corresponding gene, a heterologous promoter that is intrinsically active in cancer cells, or a heterologous promoter that can be induced by a suitable agent. Preferably, the construct is designed so that the polynucleotide sequence operably linked to the promoter is complementary to the sequence of the corresponding gene. Thus, once integrated into the cellular genome, the transcript of the administered polynucleotide will be complementary to the transcript of the gene, and capable of hybridizing with it. This approach is known as anti-sense therapy. See, for example, Culver et al. and Roth.

The use of antibodies embodied in this invention in the treatment of cancer partly relies on the fact that genes that show RNA overabundance in cancer frequently encode cell-surface proteins. Location of these proteins at the cell surface may correspond to an important biological function of the cancer cell, such as their interaction with other cells, the modulation of other cell-surface proteins, or triggering by an incoming cytokine.

These mechanisms suggest a variety of ways in which a specific antibody may be effective in decreasing the pathology of a cancer cell. For example, if the gene encodes for a growth receptor, then an antibody that blocks the ligand binding site or causes endocytosis of the receptor would decrease the ability of the receptor to provide its signal to the cell. It is unnecessary to have knowledge of the mechanism beforehand; the effectiveness of a particular antibody can be predicted empirically by testing with cultured cancer cells expressing the corresponding protein. Monoclonal antibodies may be more effective in this form of cancer therapy if several different clones directed at different determinants of the same cancer-associate gene product are used in combination: see PCT application WO 94/00136 (Kasprzyk et al.). Such antibody treatment may directly decrease the pathology of the cancer cells, or render them more susceptible to non-specific cytotoxic agents such as platinum (Lippman).

Another example of how antibodies can be used in cancer therapy is in the specific targeting of effector components. The protein product of the cancer-associated gene is expected to appear in high frequency on cancer cells compared to unaffected cells, due to the overabundance of the corresponding RNA. The protein therefore provides a marker for cancer cells that a specific antibody can bind to. An effector component attached to the antibody therefore becomes concentrated near the cancer cells, improving the effect on those cells and decreasing the effect on non-cancer cells. This concentration would generally occur not only near the primary tumor, but also near cancer cells that have metastasized to other tissue sites. Furthermore, if the antibody is able to induce endocytosis, this will enhance entry of the effector into the cell interior.

For the purpose of targeting, an antibody specific for the protein of the cancer-associated gene is conjugated with a suitable effector component, preferably by a covalent or high-affinity bond. Suitable effector components in such compositions include radionuclides such as $^{131}$I, toxic chemicals such as vincristine, and toxic peptides such as diphtheria toxin. Other suitable effector components include peptides or polynucleotides capable of altering the phenotype of the cell in a desirable fashion: for example, installing a tumor suppressor gene, or rendering them susceptible to immune attack.

In most applications of antibody molecules in human therapy, it is preferable to use human monoclonals, or antibodies that have been humanized by techniques known in the art. This helps prevent the antibody molecules themselves from becoming a target of the host's immune system.

An example of how polypeptides embodied in this invention can be effectively used in treatment is through vaccination. The growth of cancer cells is naturally limited in part due to immune surveillance. This refers to the recognition of cancer cells by immune recognition units, particularly antibodies and T cells, and the consequent triggering of immune effector functions that limit tumor progression. Stimulation of the immune system using a particular tumor-specific antigen enhances the effect towards the tumor expressing the antigen. Thus, an active vaccine comprising a polypeptide encoded by the cDNA of this invention would be appropriately administered to subjects having overabundance of the corresponding RNA. There may also be a prophylactic role for the vaccine in a population predisposed for developing cancer cells with overabundance of the same RNA.

Ways of increasing the effectiveness of cancer vaccines are known in the art (Beardsley, MacLean et al.). For example, synthetic antigens are conjugated to a carrier like keyhole limpet hemocyanin (KLH), and then combined with an adjuvant such as DETOX (TM), a mixture of mycobacterial cell walls and lipid A. Any polypeptide encoded by the four novel genes described in this invention can be used in analogous compositions.

Methods for preparing and administering polypeptide vaccines are known in the art. Peptides may be capable of eliciting an immune response on their own, or they may be rendered more immunogenic by chemical manipulation, such as cross-linking or attaching to a protein carrier like KLH. Preferably, the vaccine also comprises an adjuvant, such as alum, muramyl dipeptides, liposomes, or DETOX. The vaccine may optionally comprise auxiliary substances such as wetting agents, emulsifying agents, and organic or inorganic salts or acids. It also comprises a pharmaceutically acceptable excipient which is compatible with the active ingredient and appropriate for the route of administration. The desired dose for peptide vaccines is generally from 10 µg to 1 mg, with a broad effective latitude. The vaccine is preferably administered first as a priming dose, and then again as a boosting dose, usually at least four weeks later. Further boosting doses may be given to enhance the effect. The dose and its timing are usually determined by the person responsible for the treatment.

The foregoing detailed description provides, inter alia, a detailed explanation of how genes associated with cancer can be identified and their cDNA obtained. Polynucleotide sequences for CH1-9a11-2, CH8-2a13-1, CH13-2a12-1, and CH14-2a16-1 are provided.

The examples presented below are provided as a further guide to a practitioner of ordinary skill in the art, and are not meant to be limiting in any way.

EXAMPLES

Example 1

Selecting cDNA for Messenger RNA that is Overabundant in Breast Cancer Cells

Total RNA was isolated from each breast cancer cell line or control cell by centrifugation through a gradient of guanidine isothiocyanate/CsCl. The RNA was treated with RNase-free DNase (Promega, Madison, Wis). After extraction with phenol-chloroform, the RNA preparations were stored at −70° C. Oligo-dT polynucleotides for priming at the 3' end of messenger RNA with the sequence $T_{11}NM$ (where $N \in \{A,C,G\}$ and $M \in \{A,C,G,T\}$) were synthesized according to standard protocols. Arbitrary decamer polynucleotides (OPA01 to OPA20) for priming towards the 5' end were purchased from Operon Biotechnology, Inc., Alameda, Calif.

The RNA was reverse-transcribed using AMV reverse transcriptase (obtained from BRL) and an anchored oligo-dT primer in a volume of 20µL, according to the manufacturer's directions. The reaction was incubated at 37° C. for 60 min and stopped by incubating at 95° C. for 5 min. The cDNA obtained was used immediately or stored frozen at −70° C.

Differential display was conducted according to the following procedure: 1 µL cDNA was replicated in a total volume of 10 µL PCR mixture containing the appropriate $T_{11}NM$ sequence, 0.5 µM of a decamer primer, 200 µM dNTP, 5 µCi [$^{35}$S]-dATP (Amersham), Taq polymerase buffer with 2.5 mM $MgCl_2$ and 0.3 unit Taq polymerase (Promega). Forty cycles were conducted in the following sequence: 94° C. for 30 sec, 40° C. for 2min, 72° C. for 30 sec; and then the sample was incubated at 72° C. for 5 min. The replicated cDNA was separated on a 6% polyacrylamide sequencing gel. After electrophoresis, the gel was dried and exposed to X-ray film.

The autoradiogram was analyzed for labeled cDNA that was present in larger relative amount in all of the lanes corresponding to breast cancer cells, compared with all of the lanes corresponding to control cells. FIG. 1 provides an example of an autoradiogram from such an experiment. Lane 1 is from non-proliferating normal breast cells; lane 2 is from proliferating normal breast cells; lanes 3 to 5 are from breast cancer cell lines BT474, SKBR3, and MCF7. The left and right side shows the pattern obtained from experiments using the same $T_{11}NM$ sequence ($T_{11}AC$), but two different decamer primers. The arrows indicate the cDNA fragments that were more abundant in all three tumor lines compared with controls.

The assay illustrated in FIG. 1 was conducted using different combinations of oligo-dT primers and decamer primers. A number of differentially expressed bands were detected when different primer combinations were used. However, not all differences seen initially were reproducible after re-screening. We therefore routinely repeated each differential display for each primer combination. Only bands showing RNA overabundance in at least 2 experiments were selected for further analysis.

It is preferable to include in the differential display experiment RNA derived from uncultured normal mammary epithelial cells (termed "organoids"). These cells are obtained from surgical samples resected from healthy breast tissue, which are then coaxed apart by blunt dissection techniques and mild enzyme treatment. Using organoids as the negative control, 33 cDNA fragments were isolated from 15 displays.

Example 2
Sub-selecting cDNA that Corresponds to Genes that are Duplicated in Breast Cancer Cells cDNA fragments that were differentially expressed in the fashion described in Example 1 were excised from the dried gel and extracted by boiling at 95° C. for 10 min. Eluted cDNA was recovered by ethanol precipitation, and replicated by PCR. The product was cloned into the PCRII vector using the TA cloning system (Invitrogen).

EcoRI digested placenta DNA, and EcoRI digested DNA from the breast cancer cell lines BT474, SKBR3 and ZR-75-30 were used to prepare Southern blots to screen the cloned cDNA fragments. The cloned cDNA fragments were labeled with [32P]-dCTP, and used individually to probe the blots. A larger relative amount of binding of the probe to the lanes corresponding to the cancer cell DNA indicated that the corresponding gene had been duplicated in the cancer cells. The labeled cDNA probes were also used in Northern blots to verify that the corresponding RNA was overabundant in the appropriate cell lines.

To determine whether the cDNA fragments obtained by this selection procedure corresponded to novel genes, a partial nucleotide sequence was obtained using M13 primers. Each sequence was compared with the known sequences in Genbank. In initial experiments, 5 of the first 7 genes sequenced were mitochondrial genes. To avoid repeated isolation of mitochondrial genes, subsequent screening experiments were done with additional lanes in the DNA blot analysis for EcoRI digested and HindIII digested mitochondrial DNA. Any cDNA fragment that hybridized to the appropriate mitochondrial restriction fragments was suspected of corresponding to a mitochondrial gene, and not analyzed further.

From the 33 cDNA fragments detected from differential displays using organoid MRNA, 12 were subcloned. Of these 12, 6 detected suitable gene duplications in the appropriate cell lines. Three cDNA failed to detect duplicated genes, and 3 appeared to correspond to mitochondrial genes. Sequence analysis of the 6 suitable cDNA fragments showed no identity to any known genes.

To obtain longer cDNA corresponding to the cDNA fragments with novel sequences, the fragments were used as probes to screen a cDNA library from breast cancer cell line BT474, constructed in lambda GT10. The longer cDNA obtained from lambda GT10 were sequenced using lambda GT10 primers. The chromosomal locations of the cDNAs were determined using panels of somatic cell hybrids.

Four of the 6 novel cDNA identified so far have been processed in this fashion. The probes used to obtain the 4 new breast cancer genes are shown in Table 2.

TABLE 2

Primers used for Differential Display

| cDNA | Oligo-dT primer | Arbitrary primer |
| --- | --- | --- |
| CH1-9a11-2 | $T_{11}CC$ (SEQ ID NO: 9) | SEQ ID NO: 11 |
| CH8-2a13-1 | $T_{11}AC$ (SEQ ID NO: 10) | SEQ ID NO: 12 |
| CH13-2a12-1 | $T_{11}AC$ (SEQ ID NO: 10) | SEQ ID NO: 13 |
| CH14-2a16-1n | $T_{11}AC$ (SEQ ID NO: 10) | SEQ ID NO: 14 |

Example 3
Using the cDNA to Test Panels of Breast Cancer Cells

To determine the proportion of breast cancers in which the putative breast cancer genes were duplicated, or showed RNA overabundance without gene duplication, the four cDNA obtained according to the selection procedures described were used to probe a panel of breast cancer cell lines and primary tumors.

Gene duplication was detected either by Southern analysis or slot-blot analysis. For Southern analysis, 10 μg of EcoRI digested genomic DNA from different cell lines was electrophoresed on 0.8% agarose and transferred to a HYBOND (TM) N + membrane (Amersham). The filters were hybridized with 32P-labeled cDNA for the putative breast cancer gene. After an autoradiogram was obtained, the probe was stripped and the blot was re-probed using a reference probe to adjust for differences in sample loading. Either chromosome 2 probe D2S5 or chromosome 21 probe D21S6 was used as a reference. Densities of the signals on the autoradiograms were obtained using a densitometer (Molecular Dynamics). The density ratio between the breast cancer gene and the reference gene was calculated for each sample. Two samples of placental DNA digests were run in each Southern analysis as a control.

For slot-blot analysis, 1 itg of genomic DNA was denatured and slotted on the HYBOND (TM) membrane. D21S5 or human repetitive sequences were used as reference probes for slot blots. The density ratio between the breast cancer gene and the reference gene was calculated for each sample. 10–15 samples of placental DNA digests were used as control. Amongst the control samples, the highest density ratio was set at 1.0. The density ratio of the tumor cell lines were standardized accordingly. An arbitrary cut-off for the standardized ratio (typically 1.3) was defined to identify samples in which the putative gene had been duplicated. Each of the cell lines in the breast cancer panel was scored positively or negatively for duplication of the gene being tested.

Some of the cell lines in the panel were known to have duplicated chromosomal regions from comparative genomic hybridization analysis. In instances where the cDNA being used as probe mapped to the known amplified region, the cDNA indicated that the corresponding gene had also been duplicated. However, duplicated genes were also detected using each of the four cDNAs in instances where comparative genomic hybridization had not revealed any amplification.

Because of the nature of the technique, the standardized ratio calculated as described underestimates the gene copy number, although it is expected to rank in the same order. For example, the standardized ratio obtained for the c-myc gene in the SKBR3 breast cancer cell was 5.0. However, it is known that SKBR3 has approximately 50 copies of the c-myc gene.

To test for overabundance of RNA, 10 μg of total RNA from breast cancer cell lines or primary breast cancer tumors were electrophoresed on 0.8% agarose in the presence of the denaturant formamide, and then transferred to a nylon membrane. The membrane was probed first with 32P-labeled cDNA corresponding to the putative breast cancer gene, then stripped and reprobed with 32P-labeled cDNA for the beta-actin gene to adjust for differences in sample loading. Ratios of densities between the candidate gene and the beta-actin gene were calculated. RNA from three different cultured normal epithelial cells were included in the analysis as a control for the normal level of gene expression. The highest ratio obtained from the normal cell samples was set at 1.0, and the ratios in the various tumor cells were standardized accordingly.

Example 4
Chromosome 1 Gene CH1-9a11-2

One of the cDNA obtained through the selection procedures of Examples 1 and 2 corresponded to a gene that mapped to Chromosome 1.

Table 3 summarizes the results of the analysis for gene duplication and RNA overabundance. Both quantitative and qualitative assessment is shown. The numbers shown were obtained by comparing the autoradiograph intensity of the hybridizing band in each sample with that of the controls. Several control samples were used for the gene duplication experiments, consisting of different preparations of placental DNA. The control sample with the highest level of intensity was used for standardizing the other values. Other sources used for this analysis were breast cancer cell lines with the designations shown. For reasons stated in Example 3, the quantitative number is not a direct indication of the gene copy number, although it is expected to rank in the same order. Similarly, up to 6 control samples were used for the RNA overabundance experiments, consisting of different preparations of breast cell organoids which had been maintained briefly in tissue culture until the experiment was performed. The control sample with the highest level of intensity was used for standardizing the other values. Each cell line was scored + or − according to an arbitrary cut-off value.

TABLE 3

Chromosome 1 Gene in Breast Cancer Cell Lines

| Source | CH1-9a11-2 Gene Duplication | | CH1-9a11-2 RNA Overabundance | | | |
|---|---|---|---|---|---|---|
| | | | 5.2 kb | | 4.4 kb | |
| Normal | − | 1.00* | − | 1.00** | − | 1.0** |
| BT474 | + | 2.70 | + | 1.57 | + | 3.7 |
| ZR-75-30 | + | 2.65 | | nd | | nd |
| MDA453 | + | 2.86 | + | 5.79 | + | 6.2 |
| MDA435 | + | 3.72 | − | 0.89 | + | 2.4 |
| SKBR3 | + | 1.86 | − | 0.94 | + | 2.9 |
| 600PE | + | 1.72 | + | 4.47 | + | 6.8 |
| MDA157 | + | 1.49 | − | 1.08 | + | 1.4 |
| MCF7 | + | 1.95 | | nd | | nd |
| DU4475 | + | 2.02 | − | 1.13 | + | 1.5 |
| MDA231 | − | 1.23 | + | 1.47 | − | |
| BT20 | − | 1.09 | − | 0.83 | + | 1.9 |
| T47D | − | 1.05 | | nd | | nd |
| UACC812 | − | 0.67 | + | 1.57 | + | 1.8 |
| MDA134 | − | 1.19 | + | 5.04 | + | 7.1 |
| CAMA-1 | − | 1.02 | + | 2.51 | + | 7.2 |
| Incidence (%) | 9/15 (60%) | | 7/12 (58%) | | 11/12 (92%) | |

+ Gene duplication or RNA overabundance; − no duplication or overabundance; nd = not done
*Degree of gene duplication is reported relative to placental DNA preparations.
**Degree of RNA overabundance is reported relative to the highest level observed for several cultures of normal epithelial cells. Two hybridizing species of RNA are calculated and reported separately.

The gene corresponding to the CH1-9a11-2 cDNA was duplicated in 9 out of 15 (60%) of the breast cancer cell lines tested, compared with placental DNA digests (P3 and P12). The sequence of the 115 bases from the 5' end of the cDNA fragment (SEQ ID NO:1) showed no homology to any known gene in Genbank. One of the three possible reading frames was found to be open, with the predicted amino acid sequence of SEQ ID NO:2.

Example 5

Chromosome 8 Gene CH8-2a13-1

Figure 2:
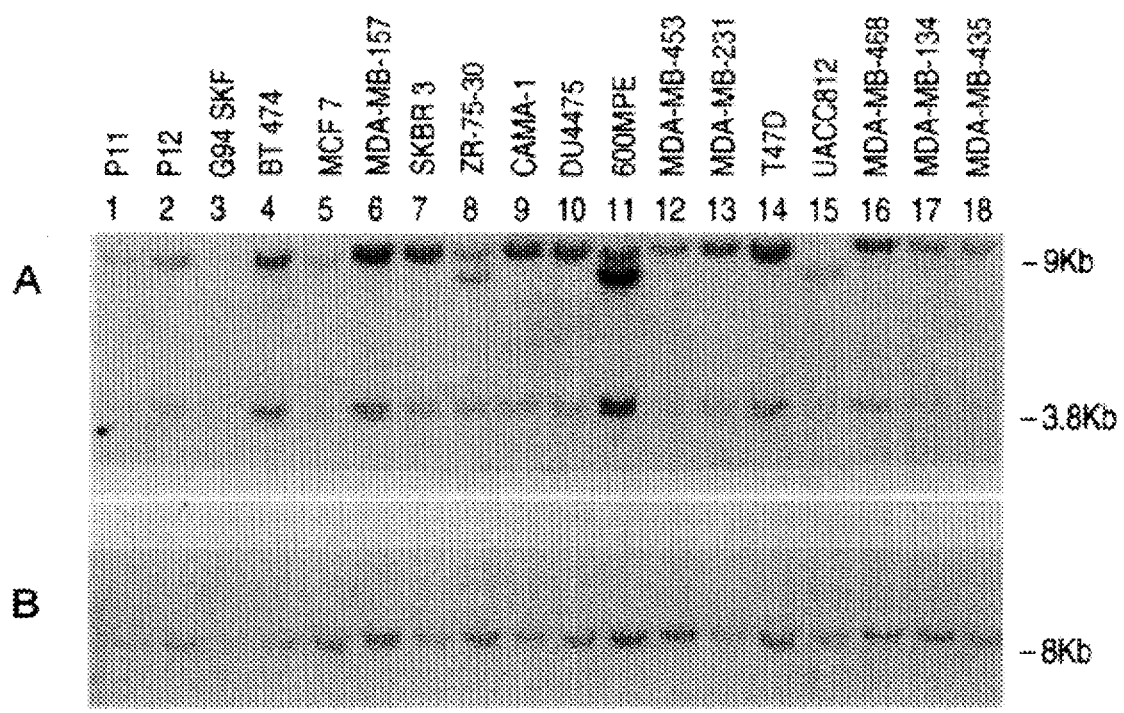
FIG. 2 is a half-tone reproduction of an autoradiogram of electrophoresed DNA digests from a panel of breast cancer cell lines probed with CH8-2a13-1 (Panel A) or a loading control (Panel B).

One of the cDNA obtained corresponded to a gene that mapped to Chromosome 8. FIG. 2 shows the Southern blot analysis for the corresponding gene in various DNA digests. Lane 1 (P12) is the control preparation of placental DNA; the rest show DNA obtained from human breast cancer cell lines. Panel A shows the pattern obtained using the 32P-labeled CH8-2a13-1 cDNA probe. Panel B shows the pattern obtained with the same blot using the 32P-labeled D2S6 probe as a loading control. The sizes of the restriction fragments are indicated on the right.

Figure 3:
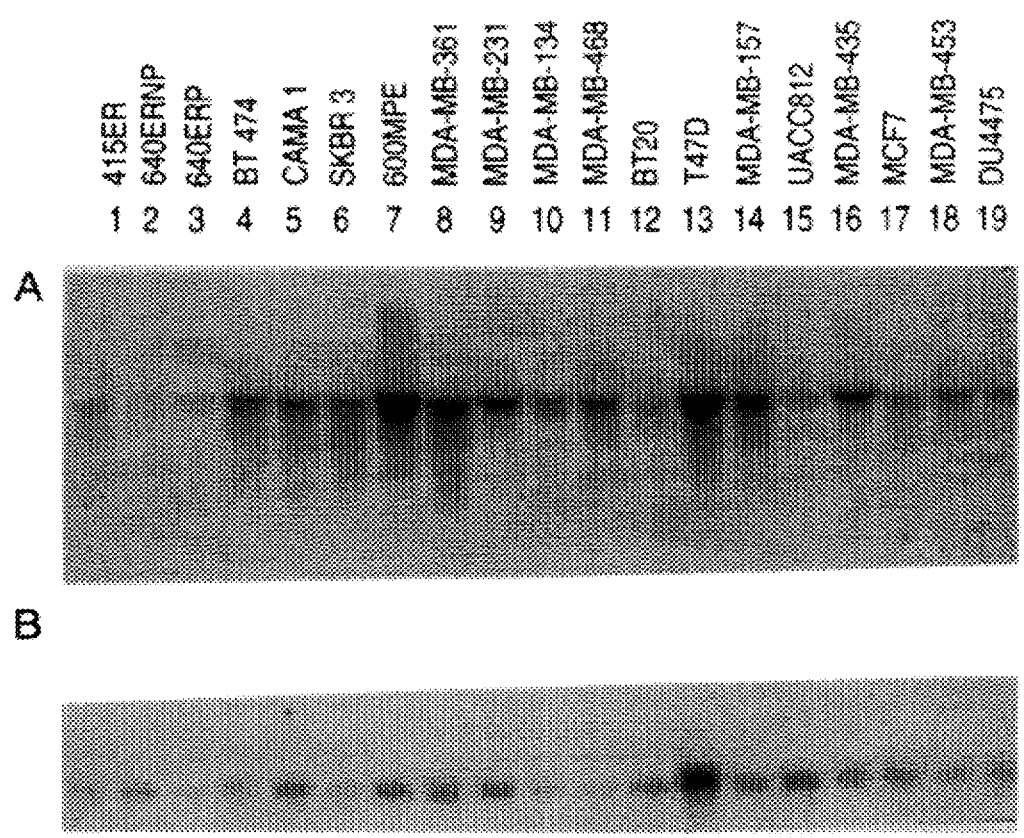
FIG. 3 is a half-tone reproduction of an autoradiogram of electrophoresed total RNA from a panel of breast cancer cell lines probed with CH8-2a13-1 (Panel A) or a loading control (Panel B).

FIG. 3 shows the Northern blot analysis for RNA overabundance. Lanes 1–3 show the level of expression in cultured normal epithelial cells. Lanes 4–19 show the level of expression in human breast cancer cell lines. Panel A shows the pattern obtained using the CH8-2a13-1 probe; panel B shows the pattern obtained with beta-actin cDNA, a loading control.

The results are summarized in Table 4. The scoring method is the same as for Example 4. The gene corresponding to CH8-2a13-1 showed clear evidence of duplication in 12 out of 17 (71%) of the cells tested. RNA overabundance was observed in 14 out of 17 (82%). Thus, 11% of the cells had achieved RNA overabundance by a mechanism other than gene duplication.

Since the known oncogene c-myc is located on Chromosome 8, the Southern analysis was also conducted using a probe for c-myc. At least 2 of the breast cancer cells showing duplication of the gene corresponding to CH8-2a13-1 gene did not show duplication of c-myc. This indicates that the gene corresponding to CH8-2a13-1 is not part of the myc amplicon.

The sequence of 150 bases from the 5' end of the cDNA fragment (SEQ ID NO:3) showed no homology to any known gene in Genbank. One of the three possible reading frames was found to be open, with the amino acid sequence of SEQ ID NO:4.

TABLE 4

Chromosome 8 Genes in Breast Cancer Cell Lines

| Source | CH8-2a13-1 Gene Duplication | | CH8-2a13-1 RNA Overabundance | | c-myc Gene Duplication | |
|---|---|---|---|---|---|---|
| Normal | − | 1.00* | − | 1.00** | − | 1.00* |
| SKBR3 | + | 4.25 | + | 4.30 | + | 4.73 |
| ZR-75-30 | + | 3.82 | nd | | + | 2.24 |
| BT474 | + | 1.53 | + | 1.72 | + | 1.76 |
| MDA157 | + | 2.02 | + | 3.39 | + | 1.39 |
| MCF7 | + | 1.84 | + | 4.92 | + | 3.10 |
| CAMA-1 | + | 3.62 | + | 2.14 | + | 1.61 |
| MDA361 | + | 2.00 | + | 1.74 | nd | |
| MDA468 | nd | | + | 4.50 | nd | |
| T47D | + | 1.41 | + | 1.58 | − | 1.02 |
| MDA453 | + | 1.83 | + | 3.10 | − | 0.90 |
| MDA134 | + | 1.30 | + | 3.70 | − | 0.88 |
| MDA435 | + | 2.15 | + | 4.94 | − | 1.00 |
| 600PE | − | 0.95 | + | 2.04 | − | 0.54 |
| UACC812 | + | 1.25 | + | 2.40 | − | 0.74 |
| MDA231 | − | 0.80 | + | 1.28 | + | 1.27 |
| DU4475 | − | 0.85 | − | 0.88 | − | 0.50 |
| BT468 | − | 0.37 | − | 0.70 | − | 0.23 |
| BT20 | − | 0.95 | − | 0.82 | − | |
| Incidence (%) | 12/17 (71%) | | 14/17 (82%) | | 7/16 (44%) | |

+ Gene duplication or RNA overabundance; − no duplication or overabundance; nd = not done.
*Degree of gene duplication is reported relative to placental DNA preparations.
**Degree of RNA overabundance is reported relative to the highest level observed for several cultures of normal epithelial cells.

Example 6

Chromosome 13 Gene CH13-2a12-1

Figure 4:
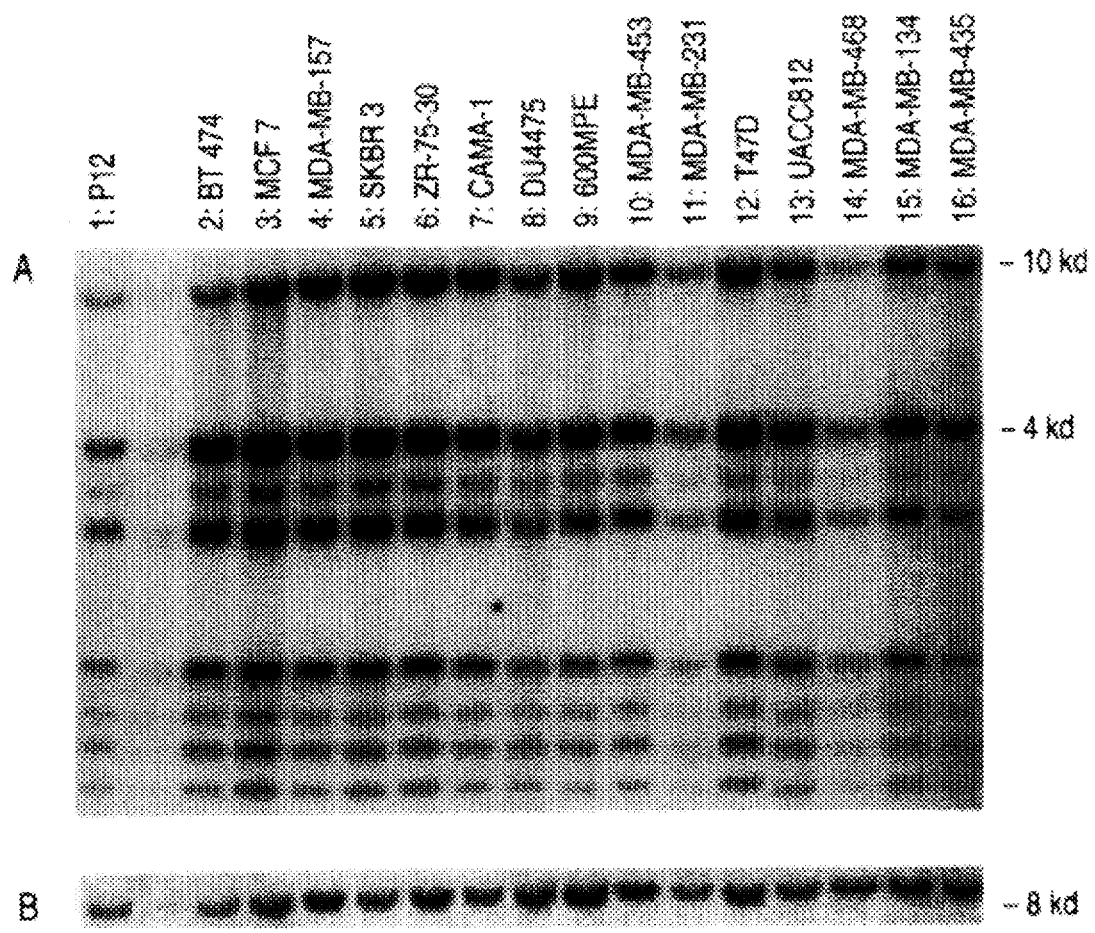
FIG. 4 is a half-tone reproduction of an autoradiogram of electrophoresed DNA digests from a panel of breast cancer cell lines probed with CH13-2a12-1.

One of the CDNA obtained corresponded to a gene that mapped to Chromosome 13. FIG. 4 shows the Southern blot analysis for the corresponding gene in various DNA digests. Lanes 1 and 2 are control preparations of placental DNA; the rest show DNA obtained from human breast cancer cell lines. Panel A shows the pattern obtained using the CH13-2a12-1 cDNA probe; panel B shows the pattern using D2S6 probe as a loading control. The sizes of the restriction fragments are indicated on the right.

Figure 5:
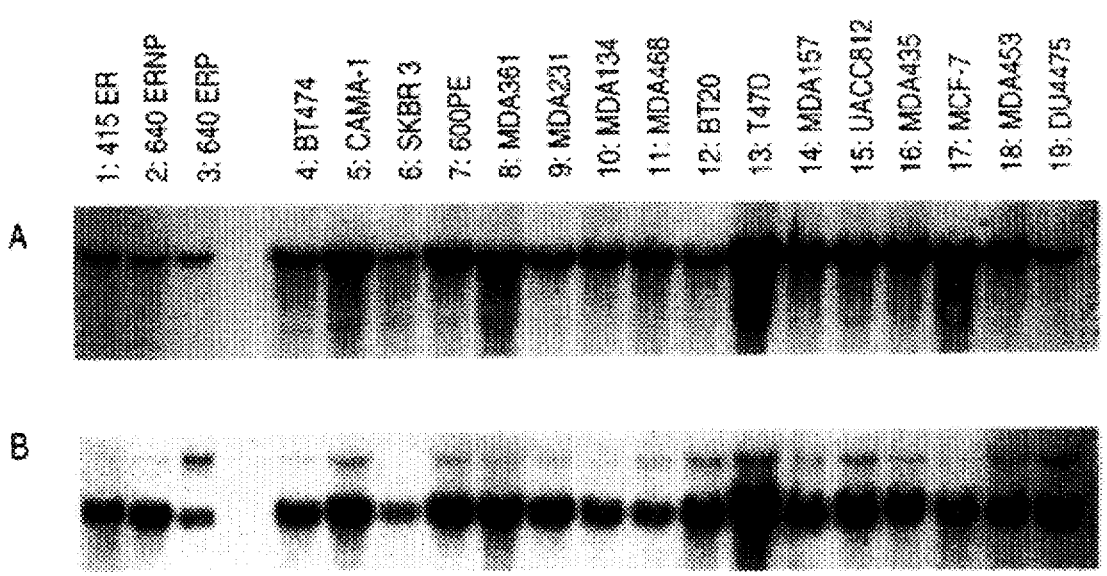
FIG. 5 is a half-tone reproduction of an autoradiogram of electrophoresed total RNA from a panel of breast cancer cell lines probed with CH13-2a12-1.

FIG. 5 shows the Northern blot analysis for RNA overabundance of the CH13-2a12-1 gene. Lanes 1–3 show the level of expression in cultured normal epithelial cells. Lanes 4–19 show the level of expression in human breast cancer cell lines. Panel A shows the pattern obtained using the CH13-2a12-1 probe; panel B shows the pattern obtained with beta-actin cDNA, a loading control.

The results are summarized in Table 5. The scoring method is the same as for Example 4. The gene corresponding to CH13-2A12-1 was duplicated in 7 out of 16 (44%) of the cells tested. Three of the positive cell lines (600PE, BT474, and MDA435) had been studied previously by comparative genomic hybridization, but had not shown amplified chromatin in the region where CH13-2A12-1 has been mapped in these studies.

RNA overabundance was observed in 13 out of 16 (81%) of the cell lines tested. Thus, 37% of the cells had achieved RNA overabundance by a mechanism other than gene duplication. We have also obtained cells from primary breast tumors, and analyzed them for duplication of the chromosome 13 gene. Ten of the 82 tumors analyzed (12%) were positive, confirming that duplication of this gene is not an artifact of in vitro culture.

The sequence of 107 bases from the 5' end of the 1.5 kb cDNA fragment (SEQ ID NO:5) showed no homology to any known gene in Genbank. One of the three possible reading frames was found to be open, with the predicted amino acid sequence of SEQ ID NO:6.

TABLE 5

| | Chromosome 13 Gene in Breast Cancer Cell Lines | | | |
|---|---|---|---|---|
| Source | CH13-2a12-1 Gene duplication | | CH13-2a12-1 RNA Overabundance | |
| Normal | – | 1.00* | – | 1.00** |
| 600PE | + | 2.18 | + | 5.57 |
| BT474 | + | 1.60 | + | 3.20 |
| SKBR3 | + | 1.58 | + | 4.25 |
| MDA157 | + | 2.21 | + | 3.76 |
| CAMA-1 | + | 1.41 | + | 1.99 |
| MDA231 | + | 1.65 | + | 2.09 |
| T47D | + | 1.23 | + | 1.20 |
| MDA468 | nd | | + | 6.90 |
| MDA361 | nd | | + | 2.59 |
| MDA435 | – | 0.59 | + | 3.41 |
| MDA134 | – | 0.53 | + | 2.59 |
| DU4475 | – | 0.75 | + | 1.79 |
| MDA453 | – | 0.89 | + | 1.97 |
| BT20 | – | 0.37 | – | 1.04 |
| MCF7 | – | 0.29 | – | 1.03 |
| UACC812 | – | 0.30 | – | 0.39 |
| BT468 | – | 0.47 | nd | |
| ZR-75-30 | – | 0.70 | nd | |
| Incidence (%) | 7/16 (44%) | | 13/16 (81%) | |

+ Gene duplication or RNA overabundance; – no duplication or overabundance; nd = not done
*Degree of gene duplication is reported relative to placental DNA preparations.
**Degree of RNA overabundance is reported relative to the highest level observed for several cultures of normal epithelial cells.

Example 7
Chromosome 14 Gene CH14-2a16-1

One of the cDNA obtained corresponded to a gene that mapped to Chromosome 14. Results of the analysis are summarized in Table 6. The scoring method is the same as for Example 4. The gene corresponding to CH14-2a16-1 was duplicated in 8 out of 15 (53%) of the cells tested. The sequence of 114 bases from the 5' end of the cDNA fragment (SEQ ID NO:7) showed no homology to any known gene in Genbank. One of the three possible reading frames was found to be open, with the predicted amino acid sequence of SEQ ID NO:8.

TABLE 6

| | Chromosome 14 Gene in Breast Cancer Cell Lines | | | |
|---|---|---|---|---|
| Source | CH14-2a16-1 Gene duplication | | CH14-2a16-1 RNA Overabundance | |
| Normal | – | 1.00* | – | 1.00** |
| BT474 | + | 2.89 | + | 2.57 |
| MCF7 | + | 1.35 | + | 1.88 |
| SKBR3 | + | 2.58 | + | 2.19 |
| T47D | + | 2.28 | nd | |
| MDA157 | + | 1.52 | + | 2.52 |
| UACC812 | + | 2.23 | nd | |
| MDA361 | – | 0.97 | + | 1.43 |
| MDA453 | + | 1.58 | + | 5.92 |
| BT20 | – | | – | 1.07 |
| 600PE | – | 0.94 | + | 2.00 |
| MDA231 | + | 1.66 | + | 2.19 |
| CAMA-1 | – | 0.92 | – | 0.71 |
| DU4475 | – | 0.87 | + | 1.33 |
| BT468 | – | 0.46 | nd | |
| MDA134 | – | 0.77 | + | 7.17 |
| Incidence (%) | 8/15 (53%) | | 10/12 (83%) | |

+ Gene duplication or overabundance; – no duplication or overabundance; nd = not done
*Degree of gene duplication is reported relative to placental DNA preparations.
**Degree of RNA overabundance is reported relative to the highest level observed for several cultures of normal epithelial cells.

REFERENCES

Publications
Adnane J. et al. (1991), "BEK and FLG, two receptors to members of the FGF family, are amplified in subsets of human breast cancers", Oncogene 6:659–661.
Alitalo K. et al. (1986), "Oncogene amplification in tumor cells", Adv. Cancer Res. 47:235–281.
Altschul et al. (1986), Bull. Math. Bio. 48:603–616.
Bauer D. et al. (1993), "Identification of differentially expressed mRNA species by an improved display technique (DDRT-PCR), Nucl. Acids Res. 21:4272–4280.
Beardsley T. (1994), "Crabshoot: manufacturers gamble on cancer vaccines again", Scientific American, September: 102.
Berns E. M. et al. (1992), "Sporadic amplification of the insulin-like growth factor 1 receptor gene in human breast tumors", Cancer Res. 52:1036–1039.
Bishop J. M. (1991), "Molecular themes in oncogenesis", Cell 64:235–248.
Blast R. C. Jr. (1993), "Perspectives on the future of cancer markers", Clin. Chem. 31:2444–2451.
Brison O. (1993), "Gene amplification and tumor progression", Biochim. Biophys. Acta 1155:25–41.
Culver K. W. et al. (1994), "Gene therapy for cancer," Trends Genet. 10:174–178.
Dutrillaux B. et al. (1990), "Characterization of chromosomal anomalies in human breast cancer", Cancer Genet Cytogenet 49:203–217.

Henikoff et al. (1992), Proc. Natl. Acad. Sci. USA 89:10915–10919.
Kallioniemi A. et al. (1992), "Comparative genomic hybridization for molecular cytogenetic analysis of solid tumors", Science 258:818–821.
Kallioniemi A. et al. (1994), "Detection and mapping of amplified DNA sequences in breast cancer by comparative genomic hybridization", Proc. Natl. Acad. Sci. USA 91:2156–2160.
Lippman M. E. (1993), "The development of biological therapies for breast cancer", Science 259:631–632.
Liang P. et al. (1992), "Differential display of eukaryotic messenger RNA by means of the polymerase chain reaction", Science 257:967–971.
Liang P. et al. (1993), "Distribution and cloning of eukaryotic mRNAs by means of differential display: refinements and optimization", Nucl. Acids Res. 21:3269–3275.
MacLean G. D. et al. (1992), "The immune system, cancer antigens and immunotherapy", Contemp. Oncol. August/September.
Muss H. B. et al. (1994), "c-erbB-2 expression and response to adjuvant therapy in women with node-positive early breast cancer", New Engl. J. Med. 330:1260–1266.
Morgan R. A. et al. (1993), "Human gene therapy," Annu. Rev. Biochem. 62:191–217.
Roth J. A. (1994), "Modulation of oncogene and tumor-suppressor gene expression: a novel strategy for cancer prevention and treatment", Ann. Surg. Oncol. 1:79–86.
Saint-Ruf C. et al. (1990), "Proto-oncogene amplification and homogeneously staining regions in human breast carcinomas", Genes Chromosomes Cancer 2:18–26.
Slamon D. J. et al. (1987), "Human breast cancer: correlation of relapse and survival with amplification of the HER-2/neu oncogene", Science 235:178–182.
Schwab M. et al. (1990), "Amplification of cellular oncogenes: a predictor of clinical outcome human cancer", Genes Chromosomes Cancer 1:181–193.
Trentmann S. M. et al. (1995), "Alternatives to $^{35}$S as a label for the differential display of eukaryotic messenger RNA", Science 267:1186–1187.
Unigned (1994), "Synthetic vaccine stabilizes advanced cancer, prolongs survival", Oncol. News 3:1.
Zafrani B. et al. (1992), "Cytogenetic study of breast cancer", Hum Pathol 23:542–547.

| U.S. patents | | | |
| --- | --- | --- | --- |
| U.S. Pat. No. 4,444,887 | 4/1984 | Hoffman M.K. | (mAB method) |
| U.S. Pat. No. 4,472,500 | 9/1984 | Milstein C. et al. | (mAB cell) |
| U.S. Pat. No. 4,491,632 | 1/1985 | Wands J.R. et al. | (HBY mAb) |
| U.S. Pat. No. 4,683,195 | 7/1987 | Mullis K.B. | (PCR) |
| U.S. Pat. No. 4,683,202 | 7/1987 | Mullis K.B. et al. | (PCR) |
| U.S. Pat. No. 4,968,603 | 11/1990 | Slamon D.J. et al. | (erbB2 in diagnosis) |
| U.S. Pat. No. 5,124,246 | 6/1992 | Urdea M.S. et al. | (branched DNA) |
| U.S. Pat. No. 5,399,346 | 21/1995 | Anderson W.F. et al. | (gene therapy) |
| Other Patents | | | |
| WO 93/08701 | 5/1993 | Goldstein, J.A. et al. | (c-myc) |
| WO 94/00136 | 1/1994 | Kasprzyk P.G. et al. | (anti-erb in therapy) |
| WO 94/00601 | 1/1994 | Levine A.J. et al. | (mAB in diagnosis) |
| WO 94/17414 | 8/1994 | Keyomarsi K. et al. | (detection) |
| WO 94/28127 | 12/1994 | Sikora K. et al. | (erb promoter) |

We claim:

1. An isolated polynucleotide of up to about 5 kb in size, comprising a linear sequence of at least 40 consecutive nucleotides at least 90% identical to a linear sequence contained in a sequence selected from the group consisting of SEQ. ID NO:3, SEQ. ID NO:5, and SEQ. ID NO:7.

2. The isolated polynucleotide of claim 1, comprising a linear sequence of at least 40 consecutive nucleotides at least 95% identical to a sequence contained in the selected sequence.

3. An isolated polynucleotide comprising a linear sequence of nucleotides identical to a sequence selected from the group consisting of SEQ. ID NO:3, SEQ. ID NO:5 and SEQ. ID NO:7.

4. A method of using a polynucleotide of claim 1 for determining gene duplication in cancerous cells, comprising the steps of:
   a) reacting DNA contained in a clinical sample with a reagent comprising the polynucleotide of claim 1, said clinical sample having been obtained from an individual suspected of having cancerous cells; and
   b) comparing the amount of complexes formed between the reagent and the DNA in the clinical sample with the amount of complexes formed between the reagent and DNA in a control sample.

5. A method of using a polynucleotide of claim 1 for determining overabundance of RNA in cancerous cells, comprising the steps of:
   a) reacting RNA contained in a clinical sample with a reagent comprising the polynucleotide of claim 1, said clinical sample having been obtained from an individual suspected of having cancerous cells; and
   b) comparing the amount of complexes formed between the reagent and the RNA in the clinical sample with the amount of complexes formed between the reagent and RNA in a control sample.

6. A diagnostic kit for determining gene duplication or RNA overabundance in cells contained in an individual as manifest in a clinical sample, comprising a reagent and a buffer in suitable packaging, wherein the reagent comprises the polynucleotide of claim 1.

7. The isolated polynucleotide of claim 1, comprising a linear sequence of at least 100 consecutive nucleotides at least 90% identical to a sequence contained in the selected sequence.

8. An isolated polynucleotide of up to about 5 kb in size, comprising a linear sequence with which a sequence of at least 40 consecutive nucleotides contained in SEQ. ID NO:3, SEQ. ID NO:5, or SEQ. ID NO:7 is 90% identical.

9. An isolated polynucleotide comprising a linear sequence of at least 40 consecutive nucleotides that hybridizes with a DNA having a sequence selected from the group consisting of SEQ. ID NO:3, SEQ. ID NO:5, and SEQ. ID NO:7 under conditions where it does not hybridize with other DNA from a human cell.

10. The isolated polynucleotide of claim 9, wherein the linear sequence is at least 100 consecutive nucleotides.

11. An isolated polynucleotide comprising a linear sequence of at least 40 consecutive nucleotides that hybridizes with an RNA having a sequence selected from the group consisting of SEQ. ID NO:3, SEQ. ID NO:5, and SEQ. ID NO:7 under conditions where it does not hybridize with other RNA from a human cell.

12. The isolated polynucleotide of claim 11, wherein the linear sequence is at least 100 consecutive nucleotides.

13. An isolated polynucleotide encoding a polypeptide comprising at least 5 consecutive amino acids identical to a sequence contained in SEQ. ID NO:4, SEQ. ID NO:6, or SEQ. ID NO:8, wherein the encoded polypeptide is immunogenic for an antibody specific for the identical sequence.

14. An isolated polynucleotide encoding at least 10 consecutive amino acids identical to a sequence contained in SEQ. ID NO:4, SEQ. ID NO:6, or SEQ. ID NO:8.

15. The isolated polynucleotide of claim 1, which is a recombinant polynucleotide.

16. The isolated polynucleotide of claim 15, which is contained in an isolated expression vector or host cell.

17. The isolated polynucleotide of claim 1, which is a polynucleotide probe or primer.

18. The isolated polynucleotide of claim 1, which is obtained by a process comprising PCR amplification.

19. The isolated polynucleotide of claim 1, which is obtained from an isolated vector.

20. A method of using a polynucleotide of claim 9, for determining gene duplication in cancerous cells, comprising the steps of:
   a) reacting DNA contained in a clinical sample with a reagent comprising the polynucleotide of claim 9, said clinical sample having been obtained from an individual suspected of having cancerous cells; and
   b) comparing the amount of complexes formed between the reagent and the DNA in the clinical sample with the amount of complexes formed between the reagent and DNA in a control sample.

21. A method of using a polynucleotide of claim 11 or determining overabundance of RNA in cancerous cells, comprising the steps of:
   a) reacting RNA contained in a clinical sample with a reagent comprising the polynucleotide of claim 11, said clinical sample having been obtained from an individual suspected of having cancerous cells; and
   b) comparing the amount of complexes formed between the reagent and the RNA in the clinical sample with the amount of complexes formed between the reagent and RNA in a control sample.

22. A set of two polynucleotides, wherein one of the polynucleotides comprises a linear sequence of at least 15 consecutive nucleotides contained in a sequence selected from SEQ. ID NO:3, SEQ. ID NO:5, and SEQ. ID NO:7, and wherein the two polynucleotides preferentially prime cell-free amplification of a polynucleotide having at least 40 consecutive nucleotides of the selected sequence compared with other human polynucleotide sequences.

23. A method of using a set of polynucleotides according to claim 22 for determining gene duplication or overabundance of RNA in cancerous cells, comprising the steps of:
   a) priming amplification of DNA or RNA in a clinical sample using the set of polynucleotides of claim 22 to yield an amplified polynucleotide, said clinical sample having been obtained from an individual suspected of having cancerous cells; and
   b) comparing the amount of polynucleotide amplified from the DNA or RNA with the amount of polynucleotide amplified from DNA or RNA from a control sample.

24. A method of screening for breast cancer associated with a gene duplication in an individual, comprising the steps of:
   a) determining gene duplication in cells from the individual according to the method of claim 20; and
   b) correlating any gene duplication determined in step a) with an increased risk for the cancer.

25. A method of screening for cancer associated with overexpression of RNA in an individual, comprising the steps of:
   a) determining overexpression of RNA in cells from the individual according to the method of claim 21; and
   b) correlating any RNA overexpression determined in step a) with an increased risk for the cancer.

26. A method of screening for cancer associated with a gene duplication or overexpression of RNA in an individual, comprising the steps of:
   a) determining gene duplication or overexpression of RNA in cells from the individual according to the method of claim 23; and
   b) correlating any gene duplication or overexpression of RNA determined in step a) with an increased risk for the cancer.

27. The method according to claim 25, wherein the cancer is breast cancer.

28. The method according to claim 26, wherein the cancer is breast cancer.

* * * * *